US012778593B2

(12) United States Patent
Eidenschink et al.

(10) Patent No.: US 12,778,593 B2
(45) Date of Patent: Nov. 3, 2026

(54) ANCHOR TIP DESIGNS FOR A MEDICAL IMPLANT FOR OCCLUDING A LEFT ATRIAL APPENDAGE

(71) Applicant: BOSTON SCIENTIFIC SCIMED, INC., Maple Grove, MN (US)

(72) Inventors: Neal Eidenschink, Wayzata, MN (US); Joshua Mark Inouye, Brooklyn Park, MN (US); Harishankar Natesan, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 190 days.

(21) Appl. No.: 18/464,394

(22) Filed: Sep. 11, 2023

(65) Prior Publication Data

US 2024/0081830 A1 Mar. 14, 2024

Related U.S. Application Data

(60) Provisional application No. 63/405,660, filed on Sep. 12, 2022.

(51) Int. Cl.
*A61B 17/12* (2006.01)

(52) U.S. Cl.
CPC .. *A61B 17/12172* (2013.01); *A61B 17/12109* (2013.01); *A61B 2017/12054* (2013.01)

(58) Field of Classification Search
CPC ...... A61B 17/12122; A61B 2017/1205; A61B 2017/00615; A61B 17/12172; A61B 17/12109; A61B 2017/12054
See application file for complete search history.

(56) References Cited

U.S. PATENT DOCUMENTS 178,283 A 6/1876 French
1,967,318 A 7/1934 Monahan
(Continued)

FOREIGN PATENT DOCUMENTS

CN 1399571 A 2/2003
CN 202143640 U 2/2012
(Continued)

OTHER PUBLICATIONS

International Search Report and Written Opinion dated Aug. 3, 2004 for International Application No. PCT/US2004/008109.
(Continued)

*Primary Examiner* — Kathleen S Holwerda
*Assistant Examiner* — James R Mcginnity
(74) *Attorney, Agent, or Firm* — Seager, Tufte & Wickhem LLP

(57) ABSTRACT

A medical implant for occluding a left atrial appendage may include an expandable framework configured to shift between a collapsed configuration and an expanded configuration. The expandable framework may include a plurality of interconnected struts and a plurality of anchor members extending radially outward from the plurality of interconnected struts in the expanded configuration. Each anchor member of the plurality of anchor members may include a base portion fixedly attached to the plurality of interconnected struts and an anchor tip portion. The anchor tip portion may include a central penetrating element and at least one tissue support element extending outward from the central penetrating element. The at least one tissue support element may be configured to be non-penetrating.

19 Claims, 13 Drawing Sheets

(56) References Cited

U.S. PATENT DOCUMENTS 3,402,710 A 9/1968 Paleschuck
3,540,431 A 11/1970 Mobin-Uddin
3,557,794 A 1/1971 Van Patten
3,638,652 A 2/1972 Kelley
3,811,449 A 5/1974 Gravlee et al.
3,844,302 A 10/1974 Klein
3,874,388 A 4/1975 King et al.
4,007,743 A 2/1977 Blake
4,108,420 A 8/1978 West et al.
4,175,545 A 11/1979 Termanini
4,309,776 A 1/1982 Berguer
4,341,218 A 7/1982 Ü
4,364,392 A 12/1982 Strother et al.
4,425,908 A 1/1984 Simon
4,545,367 A 10/1985 Tucci
4,585,000 A 4/1986 Hershenson
4,603,693 A 8/1986 Conta et al.
4,611,594 A 9/1986 Grayhack et al.
4,619,246 A 10/1986 Molgaard-Nielsen et al.
4,638,803 A 1/1987 Rand et al.
4,665,906 A 5/1987 Jervis
4,681,588 A 7/1987 Ketharanathan et al.
4,710,192 A 12/1987 Liotta et al.
4,718,417 A 1/1988 Kittrell et al.
4,759,348 A 7/1988 Cawood et al.
4,781,177 A 11/1988 Lebigot
4,793,348 A 12/1988 Palmaz
4,827,907 A 5/1989 Tashiro
4,832,055 A 5/1989 Palestrant
4,873,978 A 10/1989 Ginsburg
4,917,089 A 4/1990 Sideris
4,921,484 A 5/1990 Hillstead
4,960,412 A 10/1990 Fink
4,966,150 A 10/1990 Etienne et al.
4,998,972 A 3/1991 Chin et al.
5,037,810 A 8/1991 Saliba, Jr.
5,041,090 A 8/1991 Scheglov et al.
5,041,093 A 8/1991 Chu
5,042,707 A 8/1991 Taheri
5,053,009 A 10/1991 Herzberg
5,064,435 A 11/1991 Porter
5,071,407 A 12/1991 Termin et al.
5,078,736 A 1/1992 Behl
5,098,440 A 3/1992 Hillstead
5,108,418 A 4/1992 Lefebvre
5,108,420 A 4/1992 Marks
5,108,474 A 4/1992 Riedy et al.
5,116,360 A 5/1992 Pinchuk et al.
5,122,136 A 6/1992 Guglielmi et al.
5,133,733 A 7/1992 Rasmussen et al.
5,171,259 A 12/1992 Inoue
5,171,383 A 12/1992 Sagaye et al.
5,176,692 A 1/1993 Wilk et al.
5,192,301 A 3/1993 Kamiya et al.
5,211,658 A 5/1993 Clouse
5,234,458 A 8/1993 Metais
5,242,462 A 9/1993 El-Nounou et al.
5,256,146 A 10/1993 Ensminger et al.
5,258,000 A 11/1993 Gianturco
5,258,042 A 11/1993 Mehta
5,279,539 A 1/1994 Bohan et al.
5,284,488 A 2/1994 Sideris
5,304,184 A 4/1994 Hathaway et al.
5,306,234 A 4/1994 Johnson
5,312,341 A 5/1994 Turi
5,329,942 A 7/1994 Gunther et al.
5,334,217 A 8/1994 Das
5,344,439 A 9/1994 Otten
5,350,398 A 9/1994 Pavcnik et al.
5,350,399 A 9/1994 Erlebacher et al.
5,353,784 A 10/1994 Nady-Mohamed
5,366,460 A 11/1994 Eberbach
5,366,504 A 11/1994 Andersen et al.
5,370,657 A 12/1994 Irie
5,375,612 A 12/1994 Cottenceau et al.
5,397,331 A 3/1995 Himpens et al.
5,397,355 A 3/1995 Marin et al.
5,409,444 A 4/1995 Kensey et al.
5,417,699 A 5/1995 Klein et al.
5,421,832 A 6/1995 Lefebvre
5,425,744 A 6/1995 Fagan et al.
5,427,119 A 6/1995 Swartz et al.
5,433,727 A 7/1995 Sideris
5,443,454 A 8/1995 Tanabe et al.
5,443,478 A 8/1995 Purdy et al.
5,451,235 A 9/1995 Lock et al.
5,454,365 A 10/1995 Bonutti
5,464,408 A 11/1995 Duc
5,469,867 A 11/1995 Schmitt
5,490,856 A 2/1996 Person et al.
5,497,774 A 3/1996 Swartz et al.
5,499,975 A 3/1996 Cope et al.
5,499,995 A 3/1996 Teirstein
5,522,790 A 6/1996 Moll et al.
5,522,822 A 6/1996 Phelps et al.
5,522,836 A 6/1996 Palermo
5,527,322 A 6/1996 Klein et al.
5,527,338 A 6/1996 Purdy
5,558,093 A 9/1996 Pomeranz et al.
5,558,652 A 9/1996 Henke
5,569,204 A 10/1996 Cramer et al.
5,591,196 A 1/1997 Marin et al.
5,614,204 A 3/1997 Cochrum
5,634,936 A 6/1997 Linden et al.
5,634,942 A 6/1997 Chevillon et al.
5,637,097 A 6/1997 Yoon
5,643,282 A 7/1997 Kieturakis
5,643,292 A 7/1997 Hart
5,649,953 A 7/1997 Lefebvre
5,653,690 A 8/1997 Booth et al.
5,662,671 A 9/1997 Barbut et al.
5,669,933 A 9/1997 Simon et al.
5,681,345 A 10/1997 Euteneuer
5,681,347 A 10/1997 Cathcart et al.
5,683,411 A 11/1997 Kavteladze et al.
5,690,671 A 11/1997 McGurk et al.
5,693,067 A 12/1997 Purdy
5,695,525 A 12/1997 Mulhauser et al.
5,700,285 A 12/1997 Myers et al.
5,702,421 A 12/1997 Schneidt
5,704,910 A 1/1998 Humes
5,709,224 A 1/1998 Behl et al.
5,709,704 A 1/1998 Nott et al.
5,709,707 A 1/1998 Lock et al.
5,722,400 A 3/1998 Ockuly et al.
5,724,975 A 3/1998 Negus et al.
5,725,512 A 3/1998 Swartz et al.
5,725,552 A 3/1998 Kotula et al.
5,725,568 A 3/1998 Hastings
5,733,294 A 3/1998 Forber et al.
5,733,302 A 3/1998 Myler et al.
5,735,290 A 4/1998 Sterman et al.
5,749,880 A 5/1998 Banas et al.
5,749,883 A 5/1998 Halpern
5,749,894 A 5/1998 Engelson
5,766,219 A 6/1998 Horton
5,766,246 A 6/1998 Mulhauser et al.
5,769,816 A 6/1998 Barbut et al.
5,776,097 A 7/1998 Massoud
5,776,162 A 7/1998 Kleshinski
5,782,860 A 7/1998 Epstein et al.
5,785,679 A 7/1998 Abolfathi et al.
5,800,454 A 9/1998 Jacobsen et al.
5,800,457 A 9/1998 Gelbfish
5,800,512 A 9/1998 Letnz et al.
5,807,261 A 9/1998 Benaron et al.
5,810,874 A 9/1998 Lefebvre
5,814,028 A 9/1998 Swartz et al.
5,814,029 A 9/1998 Hassett
5,814,064 A 9/1998 Daniel
5,820,591 A 10/1998 Thompson et al.
5,823,198 A 10/1998 Jones et al.
5,830,228 A 11/1998 Knapp et al.
5,833,673 A 11/1998 Ockuly et al.

(56) References Cited

U.S. PATENT DOCUMENTS 5,836,913 A 11/1998 Orth et al.
5,836,968 A 11/1998 Simon et al.
5,840,027 A 11/1998 Swartz et al.
5,843,118 A 12/1998 Sepetka et al.
5,846,260 A 12/1998 Maahs
5,846,261 A 12/1998 Kotula et al.
5,848,969 A 12/1998 Panescu et al.
5,849,005 A 12/1998 Garrison et al.
5,851,232 A 12/1998 Lois
5,853,422 A 12/1998 Huebsch et al.
5,855,597 A 1/1999 Jayaraman
5,865,791 A 2/1999 Whayne et al.
5,865,802 A 2/1999 Yoon et al.
5,868,702 A 2/1999 Stevens et al.
5,868,708 A 2/1999 Hart et al.
5,876,367 A 3/1999 Kaganov et al.
5,879,296 A 3/1999 Ockuly et al.
5,879,366 A 3/1999 Shaw et al.
5,882,340 A 3/1999 Yoon
5,885,258 A 3/1999 Sachdeva et al.
5,891,558 A 4/1999 Bell et al.
5,895,399 A 4/1999 Barbut et al.
5,902,289 A 5/1999 Swartz et al.
5,904,680 A 5/1999 Kordis et al.
5,904,703 A 5/1999 Gilson
5,906,207 A 5/1999 Shen
5,910,154 A 6/1999 Tsugita et al.
5,911,734 A 6/1999 Tsugita et al.
5,916,236 A 6/1999 Muijs Van de Moer et al.
5,925,060 A 7/1999 Forber
5,925,063 A 7/1999 Khosravi
5,925,074 A 7/1999 Gingras et al.
5,925,075 A 7/1999 Myers et al.
5,928,192 A 7/1999 Maahs
5,928,260 A 7/1999 Chin et al.
5,931,818 A 8/1999 Werp et al.
5,935,145 A 8/1999 Villar et al.
5,935,147 A 8/1999 Kensey et al.
5,935,148 A 8/1999 Villar et al.
5,941,249 A 8/1999 Maynard
5,941,896 A 8/1999 Kerr
5,944,738 A 8/1999 Amplatz et al.
5,947,997 A 9/1999 Pavcnik et al.
5,951,589 A 9/1999 Epstein et al.
5,951,599 A 9/1999 McCrory
5,954,694 A 9/1999 Sunseri
5,954,767 A 9/1999 Pajotin et al.
5,957,940 A 9/1999 Tanner et al.
5,961,545 A 10/1999 Lentz et al.
5,976,174 A 11/1999 Ruiz
5,980,514 A 11/1999 Kupiecki et al.
5,980,555 A 11/1999 Barbut et al.
5,989,281 A 11/1999 Barbut et al.
5,993,469 A 11/1999 McKenzie et al.
5,993,483 A 11/1999 Gianotti
5,997,557 A 12/1999 Barbut et al.
6,004,280 A 12/1999 Buck et al.
6,004,348 A 12/1999 Banas et al.
6,007,523 A 12/1999 Mangosong
6,007,557 A 12/1999 Ambrisco et al.
6,010,517 A 1/2000 Baccaro
6,010,522 A 1/2000 Barbut et al.
6,013,093 A 1/2000 Nott et al.
6,024,751 A 2/2000 Lovato et al.
6,024,754 A 2/2000 Engelson
6,024,755 A 2/2000 Addis
6,024,756 A 2/2000 Huebsch et al.
6,027,520 A 2/2000 Tsugita et al.
6,033,420 A 3/2000 Hahnen
6,036,720 A 3/2000 Abrams et al.
6,042,598 A 3/2000 Tsugita et al.
6,048,331 A 4/2000 Tsugita et al.
6,051,014 A 4/2000 Jang
6,051,015 A 4/2000 Maahs
6,056,720 A 5/2000 Morse
6,063,070 A 5/2000 Eder
6,063,113 A 5/2000 Kavteladze et al.
6,066,126 A 5/2000 Li et al.
6,068,621 A 5/2000 Balceta et al.
6,074,357 A 6/2000 Kaganov et al.
6,076,012 A 6/2000 Swanson et al.
6,079,414 A 6/2000 Roth
6,080,182 A 6/2000 Shaw et al.
6,080,183 A 6/2000 Tsugita et al.
6,083,239 A 7/2000 Addis
6,090,084 A 7/2000 Hassett et al.
6,096,052 A 8/2000 Callister et al.
6,096,053 A 8/2000 Bates et al.
6,110,243 A 8/2000 Wnenchak et al.
6,123,715 A 9/2000 Amplatz
6,124,523 A 9/2000 Banas et al.
6,132,438 A 10/2000 Fleischman et al.
6,135,991 A 10/2000 Muni et al.
6,136,016 A 10/2000 Barbut et al.
6,139,527 A 10/2000 Laufer et al.
6,139,573 A 10/2000 Sogard et al.
6,152,144 A 11/2000 Lesh et al.
6,152,946 A 11/2000 Broome et al.
6,156,055 A 12/2000 Ravenscroft
6,159,195 A 12/2000 Ha et al.
6,161,543 A 12/2000 Cox et al.
6,168,615 B1 1/2001 Ken et al.
6,171,329 B1 1/2001 Shaw et al.
6,179,859 B1 1/2001 Bates et al.
6,193,739 B1 2/2001 Chevillon et al.
6,203,531 B1 3/2001 Ockuly et al.
6,206,907 B1 3/2001 Marino et al.
6,214,029 B1 4/2001 Thill et al.
6,221,092 B1 4/2001 Koike et al.
6,231,561 B1 5/2001 Frazier et al.
6,231,589 B1 5/2001 Wessman et al.
6,235,045 B1 5/2001 Barbut et al.
6,245,012 B1 6/2001 Kleshinski
6,251,122 B1 6/2001 Tsukernik
6,258,115 B1 7/2001 Dubrul
6,267,772 B1 7/2001 Mulhauser et al.
6,267,776 B1 7/2001 O'Connell
6,270,490 B1 8/2001 Hahnen
6,270,530 B1 8/2001 Eldridge et al.
6,270,902 B1 8/2001 Tedeschi et al.
6,277,138 B1 8/2001 Levinson et al.
6,285,898 B1 9/2001 Ben-Haim
6,290,674 B1 9/2001 Roue et al.
6,290,708 B1 9/2001 Kugel et al.
6,312,407 B1 11/2001 Zadno-Azizi et al.
6,319,251 B1 11/2001 Tu et al.
6,328,727 B1 12/2001 Frazier et al.
6,328,755 B1 12/2001 Marshall
6,342,062 B1 1/2002 Suon et al.
6,346,116 B1 2/2002 Brooks et al.
6,346,895 B1 2/2002 Lee et al.
6,361,545 B1 3/2002 Macoviak et al.
6,364,895 B1 4/2002 Greenhalgh
6,368,338 B1 4/2002 Kónya et al.
6,371,971 B1 4/2002 Tsugita et al.
6,375,670 B1 4/2002 Greenhalgh
6,391,044 B1 5/2002 Yadav et al.
6,398,803 B1 6/2002 Layne et al.
6,402,746 B1 6/2002 Whayne et al.
6,402,771 B1 6/2002 Palmer et al.
6,402,779 B1 6/2002 Colone et al.
6,419,669 B1 7/2002 Frazier et al.
6,440,152 B1 8/2002 Gainor et al.
6,443,972 B1 9/2002 Bosma et al.
6,447,530 B1 9/2002 Ostrovsky et al.
6,454,775 B1 9/2002 Demarais et al.
6,458,145 B1 10/2002 Ravenscroft et al.
6,464,712 B1 10/2002 Epstein et al.
6,468,291 B2 10/2002 Bates et al.
6,468,301 B1 10/2002 Amplatz et al.
6,485,501 B1 11/2002 Green
6,488,689 B1 12/2002 Kaplan et al.
6,511,496 B1 1/2003 Huter et al.
6,514,280 B1 2/2003 Gilson

(56) References Cited

U.S. PATENT DOCUMENTS

| | | | |
|---|---|---|---|
| 6,517,573 | B1 | 2/2003 | Pollock et al. |
| 6,533,782 | B2 | 3/2003 | Howell et al. |
| 6,547,760 | B1 | 4/2003 | Samson et al. |
| 6,547,815 | B2 | 4/2003 | Myers |
| 6,551,303 | B1 | 4/2003 | Van Tassel et al. |
| 6,551,344 | B2 | 4/2003 | Thill |
| 6,558,401 | B1 | 5/2003 | Azizi |
| 6,558,405 | B1 | 5/2003 | McInnes |
| 6,558,414 | B2 | 5/2003 | Layne |
| 6,562,058 | B2 | 5/2003 | Seguin et al. |
| 6,569,184 | B2 | 5/2003 | Huter |
| 6,569,214 | B2 | 5/2003 | Williams et al. |
| 6,589,214 | B2 | 7/2003 | McGuckin et al. |
| 6,589,251 | B2 | 7/2003 | Yee et al. |
| 6,599,308 | B2 | 7/2003 | Amplatz |
| 6,602,271 | B2 | 8/2003 | Adams et al. |
| 6,623,508 | B2 | 9/2003 | Shaw et al. |
| 6,641,564 | B1 | 11/2003 | Kraus |
| 6,650,923 | B1 | 11/2003 | Lesh et al. |
| 6,652,555 | B1 | 11/2003 | VanTassel et al. |
| 6,652,556 | B1 | 11/2003 | VanTassel et al. |
| 6,666,861 | B1 | 12/2003 | Grabek |
| 6,689,150 | B1 | 2/2004 | Vantassel et al. |
| 6,699,260 | B2 | 3/2004 | Dubrul et al. |
| 6,699,276 | B2 | 3/2004 | Sogard et al. |
| 6,702,825 | B2 | 3/2004 | Frazier et al. |
| 6,712,836 | B1 | 3/2004 | Berg et al. |
| 6,726,701 | B2 | 4/2004 | Gilson et al. |
| 6,730,108 | B2 | 5/2004 | Van Tassel et al. |
| 6,755,812 | B2 | 6/2004 | Peterson et al. |
| 6,827,737 | B2 | 12/2004 | Hill et al. |
| 6,837,901 | B2 | 1/2005 | Rabkin et al. |
| 6,855,153 | B2 | 2/2005 | Saadat |
| 6,911,037 | B2 | 6/2005 | Gainor et al. |
| 6,932,838 | B2 | 8/2005 | Schwartz et al. |
| 6,942,653 | B2 | 9/2005 | Quinn |
| 6,949,113 | B2 | 9/2005 | Van Tassel et al. |
| 6,958,061 | B2 | 10/2005 | Truckai et al. |
| 6,994,092 | B2 | 2/2006 | van der Burg et al. |
| 7,011,671 | B2 | 3/2006 | Welch |
| 7,014,645 | B2 | 3/2006 | Greene, Jr. et al. |
| 7,037,321 | B2 | 5/2006 | Sachdeva et al. |
| 7,044,134 | B2 | 5/2006 | Khairkhahan et al. |
| 7,097,651 | B2 | 8/2006 | Harrison et al. |
| 7,128,073 | B1 | 10/2006 | van der Burg et al. |
| 7,152,605 | B2 | 12/2006 | Khairkhahan et al. |
| 7,169,164 | B2 | 1/2007 | Borillo et al. |
| 7,179,275 | B2 | 2/2007 | McGuckin, Jr. et al. |
| 7,226,466 | B2 | 6/2007 | Opolski |
| 7,303,526 | B2 | 12/2007 | Sharkey et al. |
| 7,323,002 | B2 | 1/2008 | Johnson et al. |
| 7,597,704 | B2 | 10/2009 | Frazier et al. |
| 7,678,123 | B2 | 3/2010 | Chanduszko |
| 7,695,425 | B2 | 4/2010 | Schweich et al. |
| 7,713,282 | B2 | 5/2010 | Frazier et al. |
| 7,722,641 | B2 | 5/2010 | van der Burg et al. |
| 7,727,189 | B2 | 6/2010 | VanTassel et al. |
| 7,735,493 | B2 | 6/2010 | van der Burg et al. |
| 7,780,694 | B2 | 8/2010 | Palmer et al. |
| 7,794,472 | B2 | 9/2010 | Eidenschink et al. |
| 7,799,049 | B2 | 9/2010 | Ostrovsky et al. |
| 7,803,171 | B1 | 9/2010 | Uflacker |
| 7,811,300 | B2 | 10/2010 | Feller, III et al. |
| 7,811,314 | B2 | 10/2010 | Fierens et al. |
| 7,862,500 | B2 | 1/2011 | Khairkhahan et al. |
| 7,927,365 | B2 | 4/2011 | Fierens et al. |
| 7,959,645 | B2 | 6/2011 | Wasdyke et al. |
| 7,972,359 | B2 | 7/2011 | Kreidler |
| 8,025,495 | B2 | 9/2011 | Hardert et al. |
| 8,043,329 | B2 | 10/2011 | Khairkhahan et al. |
| 8,052,715 | B2 | 11/2011 | Quinn et al. |
| 8,062,282 | B2 | 11/2011 | Kolb |
| 8,080,032 | B2 | 12/2011 | van der Burg et al. |
| 8,097,015 | B2 | 1/2012 | Devellian |
| 8,221,384 | B2 | 7/2012 | Frazier et al. |
| 8,221,445 | B2 | 7/2012 | van Tassel et al. |
| 8,246,648 | B2 | 8/2012 | Tekulve |
| 8,287,563 | B2 | 10/2012 | Khairkhahan et al. |
| 8,323,309 | B2 | 12/2012 | Khairkhahan et al. |
| 8,388,672 | B2 | 3/2013 | Khairkhahan et al. |
| 8,491,623 | B2 | 7/2013 | Vogel et al. |
| 8,523,897 | B2 | 9/2013 | van der Burg et al. |
| 8,535,343 | B2 | 9/2013 | van der Burg et al. |
| 8,562,509 | B2 | 10/2013 | Bates |
| 8,663,273 | B2 | 3/2014 | Khairkhahan et al. |
| 8,685,055 | B2 | 4/2014 | VanTassel et al. |
| 8,740,931 | B2 | 6/2014 | Snow |
| 8,834,519 | B2 | 9/2014 | van der Burg et al. |
| 8,845,711 | B2 | 9/2014 | Miles et al. |
| 8,998,944 | B2 | 4/2015 | Thornton |
| 9,034,006 | B2 | 5/2015 | Quinn et al. |
| 9,132,000 | B2 | 9/2015 | VanTassel et al. |
| 9,168,043 | B2 | 10/2015 | van der Burg et al. |
| 9,186,152 | B2 | 11/2015 | Campbell et al. |
| 9,211,124 | B2 | 12/2015 | Campbell et al. |
| 9,445,895 | B2 | 9/2016 | Kreidler |
| 9,554,806 | B2 | 1/2017 | Larsen et al. |
| 9,561,037 | B2 | 2/2017 | Fogarty et al. |
| 9,561,097 | B1 | 2/2017 | Kim et al. |
| 9,629,636 | B2 | 4/2017 | Fogarty et al. |
| 9,700,323 | B2 | 7/2017 | Clark |
| 9,730,701 | B2 | 8/2017 | Tischler et al. |
| 9,883,936 | B2 | 2/2018 | Sutton et al. |
| 9,913,652 | B2 | 3/2018 | Bridgeman et al. |
| 9,943,299 | B2 | 4/2018 | Khairkhahan et al. |
| 9,943,315 | B2 | 4/2018 | Kaplan et al. |
| 10,071,181 | B1 | 9/2018 | Penegor et al. |
| 10,076,335 | B2 | 9/2018 | Zaver et al. |
| 10,111,645 | B2 | 10/2018 | Fearnot et al. |
| 10,143,458 | B2 | 12/2018 | Kreidler |
| 10,258,454 | B2 | 4/2019 | Molgaard-Nielsen et al. |
| 10,603,020 | B2 | 3/2020 | Rudman et al. |
| 10,939,986 | B2 | 3/2021 | Chen et al. |
| 11,039,822 | B2 | 6/2021 | Wang et al. |
| 12,280,260 | B2 * | 4/2025 | Ghosh .................... A61B 5/327 |
| 2001/0000797 | A1 | 5/2001 | Mazzocchi |
| 2001/0020181 | A1 | 9/2001 | Layne |
| 2001/0034537 | A1 | 10/2001 | Shaw et al. |
| 2001/0037141 | A1 | 11/2001 | Yee et al. |
| 2002/0022860 | A1 | 2/2002 | Borillo et al. |
| 2002/0035374 | A1 | 3/2002 | Borillo et al. |
| 2002/0045931 | A1 | 4/2002 | Sogard et al. |
| 2002/0062133 | A1 | 5/2002 | Gilson et al. |
| 2002/0082638 | A1 | 6/2002 | Porter et al. |
| 2002/0082675 | A1 | 6/2002 | Myers |
| 2002/0099439 | A1 | 7/2002 | Schwartz et al. |
| 2002/0111647 | A1 | 8/2002 | Khairkhahan et al. |
| 2002/0138094 | A1 | 9/2002 | Borillo et al. |
| 2002/0138097 | A1 | 9/2002 | Ostrovsky et al. |
| 2002/0169475 | A1 | 11/2002 | Gainor et al. |
| 2002/0177855 | A1 | 11/2002 | Greene, Jr. et al. |
| 2003/0017775 | A1 | 1/2003 | Dong et al. |
| 2003/0023262 | A1 | 1/2003 | Welch |
| 2003/0023266 | A1 | 1/2003 | Borillo et al. |
| 2003/0057156 | A1 | 3/2003 | Peterson et al. |
| 2003/0060871 | A1 | 3/2003 | Hill et al. |
| 2003/0120337 | A1 | 6/2003 | Van Tassel et al. |
| 2003/0181942 | A1 | 9/2003 | Sutton et al. |
| 2003/0191526 | A1 | 10/2003 | Van Tassel et al. |
| 2003/0195555 | A1 | 10/2003 | Khairkhahan et al. |
| 2003/0204203 | A1 | 10/2003 | Khairkhahan et al. |
| 2003/0208214 | A1 | 11/2003 | Loshakove et al. |
| 2003/0220667 | A1 | 11/2003 | van der Burg et al. |
| 2004/0034366 | A1 | 2/2004 | van der Burg et al. |
| 2004/0049210 | A1 | 3/2004 | VanTassel et al. |
| 2004/0093012 | A1 | 5/2004 | Cully et al. |
| 2004/0098031 | A1 | 5/2004 | van der Burg et al. |
| 2004/0117004 | A1 | 6/2004 | Osborne et al. |
| 2004/0122467 | A1 | 6/2004 | VanTassel et al. |
| 2004/0127935 | A1 | 7/2004 | VanTassel et al. |
| 2004/0158274 | A1 | 8/2004 | WasDyke |
| 2004/0186486 | A1 | 9/2004 | Roue et al. |
| 2004/0215230 | A1 | 10/2004 | Frazier et al. |
| 2004/0220610 | A1 | 11/2004 | Kreidler et al. |

(56) References Cited

U.S. PATENT DOCUMENTS

2004/0220682 A1 11/2004 Levine et al.
2004/0230222 A1 11/2004 van der Burg et al.
2005/0004652 A1 1/2005 van der Burg et al.
2005/0015109 A1 1/2005 Lichtenstein
2005/0038470 A1 2/2005 van der Burg et al.
2005/0049573 A1 3/2005 Van Tassel et al.
2005/0070952 A1 3/2005 Devellian
2005/0113861 A1 5/2005 Corcoran et al.
2005/0125020 A1 6/2005 Meade et al.
2005/0177182 A1 8/2005 van der Burg et al.
2005/0192627 A1* 9/2005 Whisenant ......... A61B 17/0057 606/213
2005/0203568 A1 9/2005 Burg et al.
2005/0283186 A1 12/2005 Berrada et al.
2005/0288704 A1 12/2005 Cartier et al.
2006/0015136 A1 1/2006 Besselink
2006/0030877 A1 2/2006 Martinez et al.
2006/0052816 A1 3/2006 Bates et al.
2006/0100658 A1 5/2006 Obana et al.
2006/0155323 A1 7/2006 Porter et al.
2007/0066993 A1 3/2007 Kreidler
2007/0083227 A1 4/2007 van der Burg et al.
2007/0083230 A1 4/2007 Javois
2007/0150041 A1 6/2007 Evans et al.
2007/0156123 A1 7/2007 Moll et al.
2007/0162048 A1 7/2007 Quinn et al.
2007/0185471 A1 8/2007 Johnson
2008/0275536 A1 11/2008 Zarins et al.
2009/0005803 A1 1/2009 Batiste
2009/0062841 A1 3/2009 Amplatz et al.
2009/0099647 A1 4/2009 Glimsdale et al.
2009/0105747 A1 4/2009 Chanduszko et al.
2009/0112249 A1 4/2009 Miles et al.
2009/0171386 A1 7/2009 Amplatz et al.
2009/0254195 A1 10/2009 Khairkhan et al.
2009/0318948 A1 12/2009 Linder et al.
2010/0004726 A1 1/2010 Hancock et al.
2010/0016953 A1 1/2010 Sisken et al.
2010/0049238 A1 2/2010 Simpson
2010/0106178 A1 4/2010 Obermiller et al.
2010/0256669 A1 10/2010 Harris et al.
2010/0324585 A1 12/2010 Miles et al.
2011/0054515 A1 3/2011 Bridgeman et al.
2011/0082495 A1 4/2011 Ruiz
2011/0098525 A1 4/2011 Kermode et al.
2011/0218566 A1 9/2011 Van Der Burg et al.
2011/0301630 A1 12/2011 Hendriksen et al.
2012/0029553 A1 2/2012 Quinn et al.
2012/0035643 A1 2/2012 Khairkhahan et al.
2012/0065662 A1 3/2012 Van Der Burg et al.
2012/0125619 A1 5/2012 Wood et al.
2012/0172654 A1 7/2012 Bates
2012/0172927 A1 7/2012 Campbell et al.
2012/0239077 A1 9/2012 Zaver et al.
2012/0239083 A1 9/2012 Kreidler
2012/0245619 A1 9/2012 Guest
2012/0283585 A1 11/2012 Werneth et al.
2012/0283773 A1 11/2012 Van Tassel et al.
2012/0323267 A1 12/2012 Ren
2013/0006343 A1 1/2013 Kassab et al.
2013/0012982 A1 1/2013 Khairkhahan et al.
2013/0018413 A1 1/2013 Oral et al.
2013/0110154 A1 5/2013 van der Burg et al.
2013/0131717 A1 5/2013 Glimsdale
2013/0165735 A1 6/2013 Khairkhahan et al.
2013/0178889 A1 7/2013 Miles et al.
2013/0211492 A1 8/2013 Schneider et al.
2013/0331884 A1 12/2013 Van der Burg et al.
2014/0005714 A1 1/2014 Quick et al.
2014/0018841 A1 1/2014 Peiffer et al.
2014/0039536 A1 2/2014 Cully et al.
2014/0046347 A1 2/2014 Cully et al.
2014/0046360 A1 2/2014 van der Burg et al.
2014/0081314 A1 3/2014 Zaver et al.
2014/0100596 A1 4/2014 Rudman et al.
2014/0142612 A1 5/2014 Li et al.
2014/0148842 A1 5/2014 Khairkhahan et al.
2014/0163605 A1 6/2014 VanTassel et al.
2014/0188157 A1 7/2014 Clark
2014/0303719 A1 10/2014 Cox et al.
2014/0336612 A1 11/2014 Frydlewski et al.
2014/0336699 A1 11/2014 van der Burg et al.
2015/0005810 A1 1/2015 Center et al.
2015/0039021 A1 2/2015 Khairkhahan et al.
2015/0080903 A1 3/2015 Dillard et al.
2015/0196300 A1 7/2015 Tischler et al.
2015/0230909 A1 8/2015 Zaver et al.
2015/0238197 A1 8/2015 Quinn et al.
2015/0305727 A1 10/2015 Karimov et al.
2015/0313604 A1 11/2015 Roue et al.
2015/0313605 A1 11/2015 Griffin
2015/0327979 A1 11/2015 Quinn et al.
2015/0374491 A1 12/2015 Kreidler
2016/0051358 A1 2/2016 Sutton et al.
2016/0058539 A1 3/2016 VanTassel et al.
2016/0066922 A1 3/2016 Bridgeman et al.
2016/0106437 A1 4/2016 van der Burg et al.
2016/0192942 A1 7/2016 Strauss et al.
2016/0287259 A1 10/2016 Hanson et al.
2016/0331382 A1 11/2016 Center et al.
2016/0374657 A1 12/2016 Kreidler
2017/0027552 A1 2/2017 Turkington et al.
2017/0042550 A1 2/2017 Chakraborty et al.
2017/0056166 A1 3/2017 Ratz et al.
2017/0095238 A1* 4/2017 Rudman ............ A61B 17/1214
2017/0100112 A1 4/2017 van der Burg et al.
2017/0119400 A1 5/2017 Amplatz et al.
2017/0181751 A1 6/2017 Larsen et al.
2017/0340336 A1 11/2017 Osypka
2018/0064446 A1 3/2018 Figulla et al.
2018/0070950 A1 3/2018 Zaver et al.
2018/0140412 A1 5/2018 Sutton et al.
2018/0140413 A1 5/2018 Quinn et al.
2018/0250014 A1 9/2018 Melanson et al.
2018/0310925 A1 11/2018 Inouye et al.
2019/0046213 A1 2/2019 Gong et al.
2019/0083224 A1 3/2019 Tessmer
2019/0091023 A1 3/2019 Starksen et al.
2019/0117367 A1 4/2019 Simpson
2019/0125362 A1 5/2019 Tischler
2019/0167242 A1 6/2019 Rowe et al.
2019/0223883 A1 7/2019 Anderson et al.
2019/0298332 A1 10/2019 Khairkhahan et al.
2019/0298380 A1 10/2019 Inouye et al.
2019/0299011 A1 10/2019 Chu
2020/0008812 A1* 1/2020 Inouye ............. A61B 17/12172
2020/0060801 A1 2/2020 Yang
2020/0060849 A1 2/2020 Inouye et al.
2020/0178981 A1 6/2020 Anderson et al.
2021/0015596 A1 1/2021 Nigon
2021/0059685 A1 3/2021 Groff et al.
2021/0085463 A1 3/2021 Yellin et al.
2021/0161664 A1 6/2021 Krumpelmann et al.
2021/0205082 A1 7/2021 Whitman
2021/0322164 A1 10/2021 Schweich, Jr. et al.
2022/0110747 A1 4/2022 Morriss et al.
2022/0280166 A1* 9/2022 Morin .............. A61B 17/12177
2023/0071725 A1 3/2023 Inouye
2023/0142374 A1 5/2023 Inouye

FOREIGN PATENT DOCUMENTS

CN 106859722 A 6/2017
DE 10201004476 A1 3/2012
EP 1523957 A2 4/2005
EP 1595504 A1 11/2005
EP 2074953 A1 1/2009
EP 2481381 A1 8/2012
EP 2928420 A1 10/2015
EP 3072461 A1 9/2016
EP 3372173 A2 9/2018
JP 2003532457 A 11/2003
JP 2005324019 A 11/2005
JP 2007513684 A 5/2007

(56) References Cited

FOREIGN PATENT DOCUMENTS

| | | | |
|---|---|---|---|
| JP | 2009160402 | A | 7/2009 |
| JP | 2012501793 | A | 1/2012 |
| WO | 9313712 | A1 | 7/1993 |
| WO | 9504132 | A1 | 2/1995 |
| WO | 9522359 | A1 | 8/1995 |
| WO | 9601591 | A1 | 1/1996 |
| WO | 9640356 | A1 | 12/1996 |
| WO | 9721402 | A1 | 6/1997 |
| WO | 9726939 | A1 | 7/1997 |
| WO | 9728749 | A1 | 8/1997 |
| WO | 9735522 | A1 | 10/1997 |
| WO | 9802100 | A1 | 1/1998 |
| WO | 9817187 | A1 | 4/1998 |
| WO | 9822026 | A1 | 5/1998 |
| WO | 9823322 | A1 | 6/1998 |
| WO | 9827868 | A1 | 7/1998 |
| WO | 9905977 | A1 | 2/1999 |
| WO | 9907289 | A1 | 2/1999 |
| WO | 9908607 | A1 | 2/1999 |
| WO | 9923976 | A1 | 5/1999 |
| WO | 9925252 | A1 | 5/1999 |
| WO | 9930640 | A1 | 6/1999 |
| WO | 9944510 | A1 | 9/1999 |
| WO | 9959479 | A1 | 11/1999 |
| WO | 0001308 | A1 | 1/2000 |
| WO | 0016705 | A1 | 3/2000 |
| WO | 0027292 | A1 | 5/2000 |
| WO | 0035352 | A1 | 6/2000 |
| WO | 0053120 | A1 | 9/2000 |
| WO | 0067669 | A1 | 11/2000 |
| WO | 0108743 | A1 | 2/2001 |
| WO | 0115629 | A1 | 3/2001 |
| WO | 0121247 | A1 | 3/2001 |
| WO | 0126726 | A1 | 4/2001 |
| WO | 0130266 | A1 | 5/2001 |
| WO | 0130267 | A1 | 5/2001 |
| WO | 0130268 | A1 | 5/2001 |
| WO | 0170119 | A1 | 9/2001 |
| WO | 0215793 | A2 | 2/2002 |
| WO | 0224106 | A2 | 3/2002 |
| WO | 02071977 | A2 | 9/2002 |
| WO | 03007825 | A1 | 1/2003 |
| WO | 03008030 | A2 | 1/2003 |
| WO | 03032818 | A1 | 4/2003 |
| WO | 2004012629 | A1 | 2/2004 |
| WO | 2007044536 | A1 | 4/2007 |
| WO | 2010024801 | A1 | 3/2010 |
| WO | 2010081033 | A1 | 7/2010 |
| WO | 2013060855 | A1 | 5/2013 |
| WO | 2013159065 | A1 | 10/2013 |
| WO | 2014011865 | A1 | 1/2014 |
| WO | 2014018907 | A1 | 1/2014 |
| WO | 2014078698 | A2 | 5/2014 |
| WO | 2014089129 | A1 | 6/2014 |
| WO | 2014106239 | A1 | 7/2014 |
| WO | 2015164836 | A1 | 10/2015 |
| WO | 2016087145 | A1 | 6/2016 |
| WO | 2018017935 | A1 | 1/2018 |
| WO | 2018187732 | A1 | 10/2018 |
| WO | 2019084358 | A1 | 5/2019 |
| WO | 2021052486 | A1 | 3/2021 |

OTHER PUBLICATIONS

International Search Report and Written Opinion dated Feb. 15, 2000 for International Application No. PCT/US99/26325.
International Search Report dated May 20, 2003 for International Application No. PCT/US02/33808.
Written Opinion dated Nov. 17, 2003 for International Application No. PCT/US/02/33808.
International Search Report and Written Opinion dated Aug. 21, 2018 for International Application No. PCT/US2018/029684.
Cragg et al., "A New Percutaneous Vena Cava Filter," American Journal of Radiology, Sep. 1983, pp. 601-604, vol. 141.
Cragg et al., "Nonsurgical Placement of Arterial Endoprostheses: A New Technique Using Nitinol Wire," Radiology, Apr. 1983, pp. 261-263, vol. 147, No. 1.
Lock et al., "Transcatheter Closure of Atrial Septal Defects." Circulation, May 1989, pp. 1091-1099, vol. 79, No. 5.
Lock et al., "Transcatheter Umbrella Closure of Congenital Heart Defects," Circulation, Mar. 1987, pp. 593-599, vol. 75, No. 3.
Rashkind et al., "Nonsurgical closure of patent ductus arteriosus: clinical application of the Rashkind PDA Occluder System," Circulation, Mar. 1987, pp. 583-592, vol. 75, No. 3.
Rosengart et al., "Percutaneous and Minimally Invasive Valve Procedures," Circulation, Apr. 1, 2008, pp. 1750-1767, vol. 117.
Ruttenberg, "Nonsurgical Therapy of Cardiac Disorders," Pediatric Consult, 1986, Pages not numbered, vol. 5, No. 2.
Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.
Wessel et al., "Outpatient Closure of the Patent Ductus Arteriousus," Circulation, 1988, pp. 1068-1071, vol. 77, No. 5.
Tung et al., U.S. Appl. No. 61/559,941, filed Nov. 15, 2011.
Yue Yu et al., U.S. Appl. No. 61/557,880, filed Dec. 20, 2011.
Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.
International Search Report and Written Opinion dated Apr. 22, 2014 for International Application No. PCT/US2013/078454.
Aryana et al., "Incomplete Closure of the Left Atrial Appendage: Implication and Management." Curr Cardiol Rep., 18(9):82, 2016.
Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.
University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.
Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.
Romero et al., "Left Atrial Appendage Closure Devices," Clinical Medicine Insights: Cardiology, vol. 8, pp. 45-52, 2014.
Invitation to Pay Additional Fees and, Where Applicable, Protest Fee, for International Application No. PCT/US2016/043363, mailed Oct. 13, 2016.
International Search Report and Written Opinion dated Oct. 14, 2019 for International Application No. PCT/US2019/047452.
International Search Report and Written Opinion dated Oct. 27, 2017 for International Application No. PCT/US2017/048150.
International Search Report and Written Opinion dated Jan. 21, 2019 for International Application No. PCT/US2018/051953.
International Search Report and Written Opinion dated Oct. 13, 2016 for International Application No. PCT/US2016/043363.
International Search Report and Written Opinion dated Mar. 17, 20, for International Application No. PCT/US2019/065243.
International Search Report and Written Opinion dated Sep. 9, 2019 for International Application No. PCT/US2019/033698.
Blackshear et al.; "Appendage Obliteration to Reduce Stroke in Cardiac Surgical Patients with Atrial Fibrillation", Ann. Thoracic Surgery, pp. 755-759, 1996.
Lindsay, "Obliteration of the Left Atrial Appendage: A Concept Worth Testing", Ann. Thoracic Surgery, 1996.
Invitation to Pay Additional Fees dated Feb. 22, 2019 for International Application No. PCT/US2018/066163.
International Search Report and Written Opinion dated Oct. 23, 2020 for International Application No. PCT/US2020/042192.
International Search Report and Written Opinion dated Dec. 6, 2022 for International Application No. PCT/US2022/042696.
LabCE. https://www.labce.com/spg579126_red_blood_cell_rbc_size_variation.aspx. "Red Blood Cell (RBC) Size Variation", 2019.
International Search Report and Written Opinion dated Feb. 23, for International Application No. PCT/US2022/04980.

(56) References Cited

OTHER PUBLICATIONS

Invitation to Pay Additional Fees Received for PCT Patent Application No. PCT/US2023/073823, mailed on Nov. 30, 2023. (24 pages).

* cited by examiner

ANCHOR TIP DESIGNS FOR A MEDICAL IMPLANT FOR OCCLUDING A LEFT ATRIAL APPENDAGE

CROSS REFERENCE TO RELATED APPLICATIONS

This application claims the benefit of priority of U.S. Provisional Application No. 63/405,660 filed Sep. 12, 2022, the entire disclosure of which is hereby incorporated by reference.

TECHNICAL FIELD

The present disclosure pertains to medical devices and systems, and methods for manufacturing and using medical devices and systems. More particularly, the present disclosure pertains to medical implants for occluding a left atrial appendage and anchoring tip designs for said medical implants.

BACKGROUND

Diseases and/or medical conditions that impact the cardiovascular system are prevalent throughout the world. Traditionally, treatment of the cardiovascular system was often conducted by directly accessing the impacted part of the system. More recently, less invasive therapies have been developed, and have gained wide acceptance among patients and clinicians.

Atrial fibrillation is a common sustained cardiac arrhythmia affecting over 30 million people worldwide, according to some estimates. Atrial fibrillation is the irregular, chaotic beating of the upper chambers of the heart. Electrical impulses discharge so rapidly that the atrial muscle quivers or fibrillates. Episodes of atrial fibrillation may last a few minutes or several days. The most serious consequence of atrial fibrillation is ischemic stroke. It has been estimated that up to 20% of all strokes are related to atrial fibrillation. Most atrial fibrillation patients, regardless of the severity of their symptoms or frequency of episodes, require treatment to reduce the risk of stroke. The left atrial appendage is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage.

The disclosure relates to medical implants for occluding the left atrial appendage. Of the known medical devices, systems, and methods, each has certain advantages and disadvantages. There is an ongoing need to provide alternative medical devices and systems, as well as alternative methods for manufacturing and using medical devices and systems.

SUMMARY

In one example, a medical implant for occluding a left atrial appendage may comprise an expandable framework configured to shift between a collapsed configuration and an expanded configuration. The expandable framework may include a plurality of interconnected struts and a plurality of anchor members extending radially outward from the plurality of interconnected struts in the expanded configuration. Each anchor member of the plurality of anchor members may include a base portion fixedly attached to the plurality of interconnected struts and an anchor tip portion. The anchor tip portion may include a central penetrating element and at least one tissue support element extending outward from the central penetrating element. The at least one tissue support element may be configured to be non-penetrating.

In addition or alternatively to any example described herein, the at least one tissue support element is disposed symmetrically about a central axis of the central penetrating element.

In addition or alternatively to any example described herein, the at least one tissue support element extends circumferentially about the central axis of the central penetrating element.

In addition or alternatively to any example described herein, the at least one tissue support element is configured to shift radially outward from the central penetrating element as the at least one tissue support element engages tissue.

In addition or alternatively to any example described herein, the at least one tissue support element includes a hollow interior space.

In addition or alternatively to any example described herein, the anchor tip portion extends in a first direction from a curved portion of each anchor member, the curved portion extending from the base portion to the anchor tip portion.

In addition or alternatively to any example described herein, the central penetrating element extends in the first direction to a free end.

In addition or alternatively to any example described herein, the at least one tissue support element extends outward and in the first direction from an intersection of the at least one tissue support element and the central penetrating element.

In addition or alternatively to any example described herein, the at least one tissue support element is concave, and the central penetrating element extends in the first direction from inside the at least one tissue support element.

In addition or alternatively to any example described herein, the at least one tissue support element is monolithically formed with the central penetrating element.

In addition or alternatively to any example described herein, the central penetrating element has a generally conical shape.

In addition or alternatively to any example described herein, a medical device system may comprise a catheter, a core wire movably disposed within a lumen of the catheter, and a medical implant for occluding a left atrial appendage releasably connected to a distal portion of the core wire. The medical implant may include an expandable framework configured to shift between a collapsed configuration and an expanded configuration. The expandable framework may include a plurality of interconnected struts and a plurality of anchor members extending radially outward from the plurality of interconnected struts in the expanded configuration. Each anchor member of the plurality of anchor members may include a base portion fixedly attached to the plurality of interconnected struts and an anchor tip portion. The anchor tip portion may include a central penetrating element and at least one tissue support element extending outward from the central penetrating element. The at least one tissue support element may be configured to be non-penetrating.

In addition or alternatively to any example described herein, the medical implant includes an occlusive element secured to the expandable framework.

In addition or alternatively to any example described herein, the at least one tissue support element is configured to prevent the central penetrating element from penetrating completely through a wall of the left atrial appendage.

In addition or alternatively to any example described herein, a medical implant for occluding a left atrial appendage may comprise an expandable framework configured to shift between a collapsed configuration and an expanded configuration. The expandable framework may include a plurality of interconnected struts and a plurality of anchor members extending radially outward from the plurality of interconnected struts in the expanded configuration. Each anchor member of the plurality of anchor members may include a base portion fixedly attached to the plurality of interconnected struts, an anchor tip portion, and a curved portion extending radially outward from the base portion to the anchor tip portion when the expandable framework is in the expanded configuration. The anchor tip portion may include a central penetrating element configured to penetrate into a wall of the left atrial appendage and at least one tissue support element configured to engage the wall of the left atrial appendage, the at least one tissue support element extending radially outward from the central penetrating element. The anchor tip portion may be devoid of any element configured to penetrate into the wall of the left atrial appendage other than the central penetrating element.

In addition or alternatively to any example described herein, the at least one tissue support element extends circumferentially around the central penetrating element.

In addition or alternatively to any example described herein, the at least one tissue support element is symmetric about the central penetrating element.

In addition or alternatively to any example described herein, the at least one tissue support element includes a concave portion opening toward a free end of the central penetrating element.

In addition or alternatively to any example described herein, the at least one tissue support element includes a plurality of notches formed around a perimeter of the concave portion.

In addition or alternatively to any example described herein, each notch of the plurality of notches opens toward the free end of the central penetrating element.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
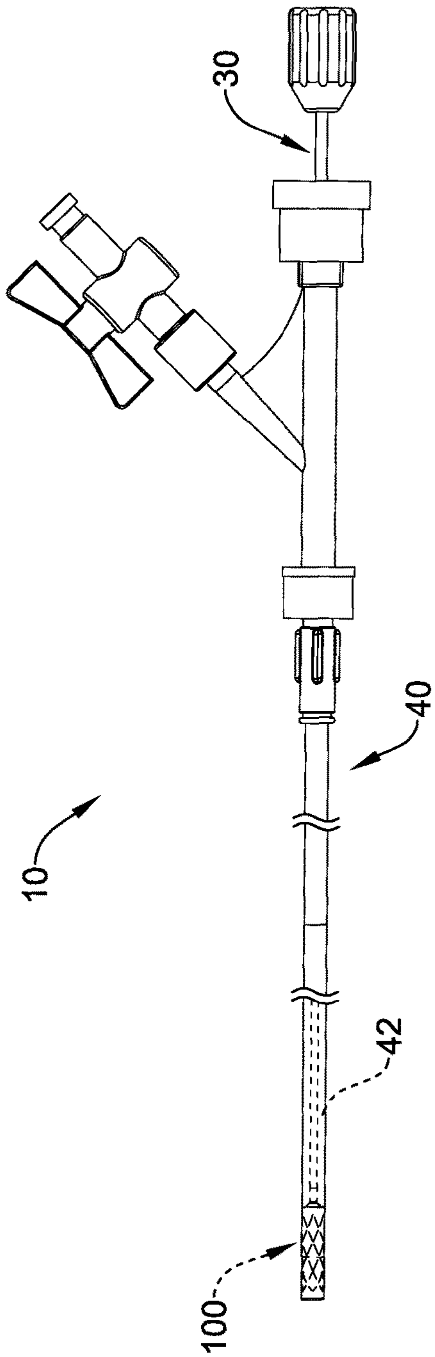
FIGS. 1-2 are side views of an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate exemplary aspects of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. It shall be understood that the discussion(s) herein may apply equally to any and/or all of the components for which there are more than one, unless explicitly stated to the contrary.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean the maximum outer dimension, "radial extent" may be understood to mean the maximum radial dimension, "longitudinal extent" may be understood to mean the maximum longitudinal dimension, etc. Each instance of an "extent" may be different (e.g., axial, longitudinal, lateral, radial, circumferential, etc.) and will be apparent to the skilled person from the context of the individual usage. In some instances, an "extent" may be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of medical implants, systems, and methods of manufacturing the same. It should be noted that in any given figure, some features of the medical implants, systems, and methods may not be shown, or may be shown schematically, for simplicity. Additional details regarding some elements may be illustrated in other figures in greater detail. The devices and/or methods disclosed herein may provide a number of desirable features and benefits as described in more detail below.

Figure 2:
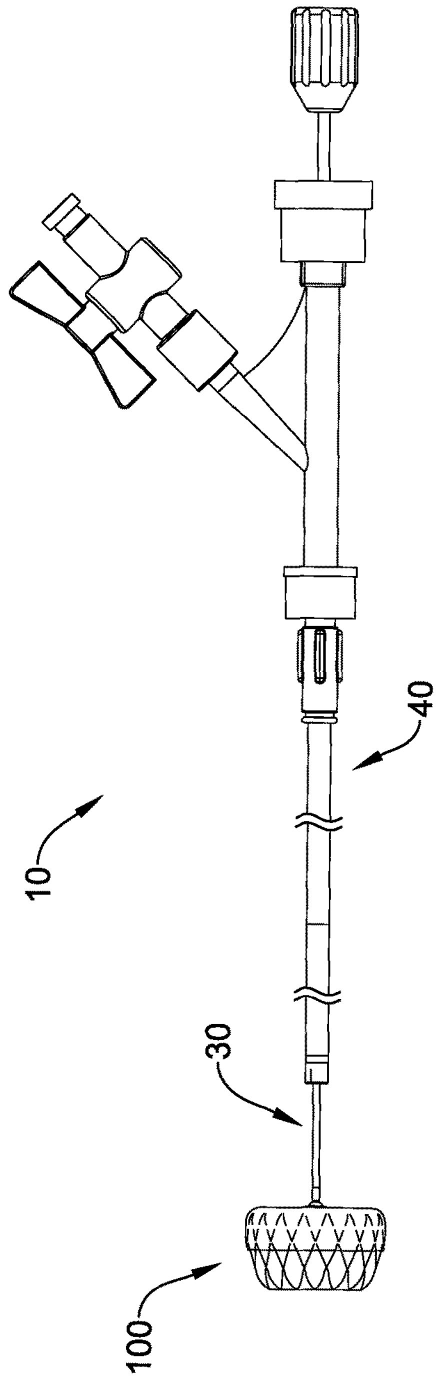

FIGS. 1-2 schematically illustrate selected components and/or arrangements of a medical device system 10. The medical device system 10 may be used to deliver and/or deploy a variety of medical implants (e.g., a cardiovascular medical implant, an occlusive medical implant, etc.) to one or more locations within the anatomy of a patient including but not limited to the heart and/or the vasculature.

The medical device system 10 may include a catheter 40 having a lumen 42 extending from a proximal opening to a distal opening, a core wire 30 movably and/or slidably disposed within the lumen 42, and a medical implant 100 (e.g., a cardiovascular medical implant, an occlusive medical implant, etc.). The medical implant 100 may be configured to occlude the left atrial appendage of the patient.

The medical implant 100 may include an expandable framework configured to shift between a collapsed configuration (e.g., FIG. 1), wherein the medical implant 100 is disposed within the lumen 42 proximate the distal opening in the collapsed configuration, and an expanded configuration (e.g., FIG. 2), wherein the medical implant 100 and/or the expandable framework is configured to shift between the collapsed configuration and the expanded configuration when the medical implant 100 is disposed distal of the distal opening of the lumen 42 and/or the catheter 40, and/or when the medical implant 100 is unconstrained by the catheter 40.

The medical implant 100 may be disposed at and/or releasably connected to a distal portion of the core wire 30. In some embodiments, the medical implant 100 may be releasably connected to the distal end of the core wire 30. The core wire 30 may be slidably and/or rotatably disposed within the lumen 42 of the catheter 40. In some embodiments, a proximal end of the core wire 30 may extend proximally of a proximal end of the catheter 40 and/or the proximal opening of the lumen 42 for manual manipulation by a clinician or practitioner.

Some suitable, but non-limiting, examples of materials for the medical device system 10, the core wire 30, the catheter 40, and/or the medical implant 100, etc. are discussed below. It is contemplated that any and/or all medical implants disclosed herein may be used in accordance with and/or be associated with the medical device system 10 described above.

Figure 3:
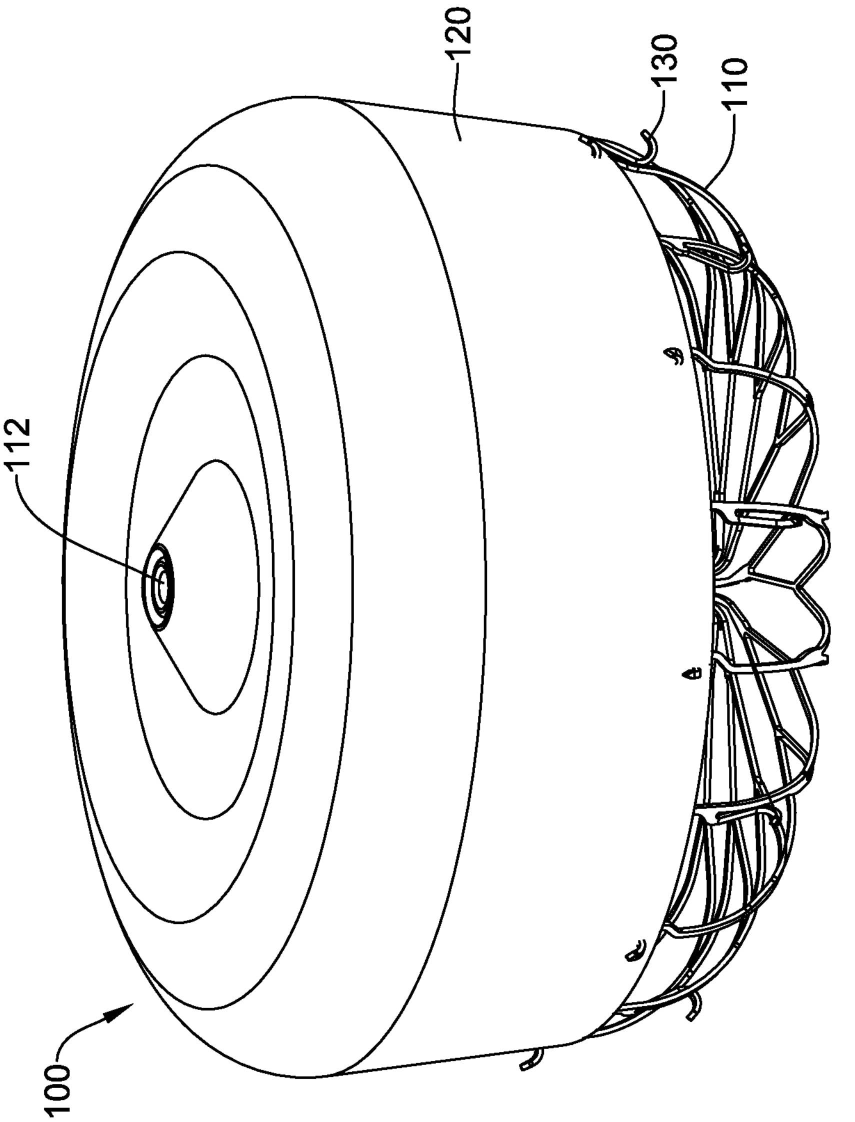
FIG. 3 is a perspective view of a medical implant of the medical device system.

FIG. 3 illustrates selected aspects of the medical implant 100. The medical implant 100 includes an expandable framework 110 configured to shift between the collapsed configuration (e.g., FIG. 1) and the expanded configuration (e.g., FIGS. 2, 3). In some embodiments, the expandable framework 110 may include a plurality of interconnected struts. In some embodiments, the expandable framework 110 may include a proximal hub 112 and the plurality of interconnected struts may extend from the proximal hub 112. In some embodiments, the expandable framework 110 may include the proximal hub 112, a distal hub (not shown), and the plurality of interconnected struts may extend between the proximal hub 112 and the distal hub.

The expandable framework 110 may have a longitudinal axis extending through the proximal hub 112. In some embodiments, the longitudinal axis may extend from the proximal hub 112 to the distal hub. The proximal hub 112 of the expandable framework 110 may be configured to releasably attach or connect to the distal end of the core wire 30. The proximal hub 112 of the expandable framework 110 may include a threaded insert fixedly attached to the expandable framework 110, the threaded insert being configured to engage a threaded member disposed at the distal end of the core wire 30 of the medical device system 10 to releasably connect the medical implant 100 to the distal end of the core wire 30. The expandable framework 110 may be disposed in the collapsed configuration when the medical implant 100 is disposed within the lumen 42 of the catheter 40 of the medical device system 10. The expandable framework 110 may be configured to shift toward the expanded configuration when the medical implant 100 is disposed outside of the lumen 42 of the catheter 40 of the medical device system 10 and/or when the medical implant 100 and/or the expandable framework 110 is unconstrained by the catheter 40.

In some embodiments, the medical implant 100 may include an occlusive element 120 disposed on and/or secured to the expandable framework 110 and/or the plurality of interconnected struts. In some embodiments, the occlusive element 120 may include a membrane, a mesh, a porous fabric, or other material configured to promote occlusion of the left atrial appendage and/or configured to promote endothelial ingrowth. In some embodiments, the occlusive element 120 may be disposed on, along, and/or over an exterior surface of the expandable framework 110. In some embodiments, the occlusive element 120 may cover at least 20% of the expandable framework 110 in the second configuration. In some embodiments, the occlusive element 120 may cover at least 30% of the expandable framework 110 in the second configuration. In some embodiments, the occlusive element 120 may cover at least 40% of the expandable framework 110 in the second configuration. In some embodiments, the occlusive element 120 may cover at least 50% of the expandable framework 110 in the second configuration. In some embodiments, the occlusive element 120 may cover at least 60% of the expandable framework 110 in the second configuration. In some embodiments, the occlusive element 120 may cover at least 70% of the expandable framework 110 in the second configuration. Other configurations are also contemplated.

Figure 4:
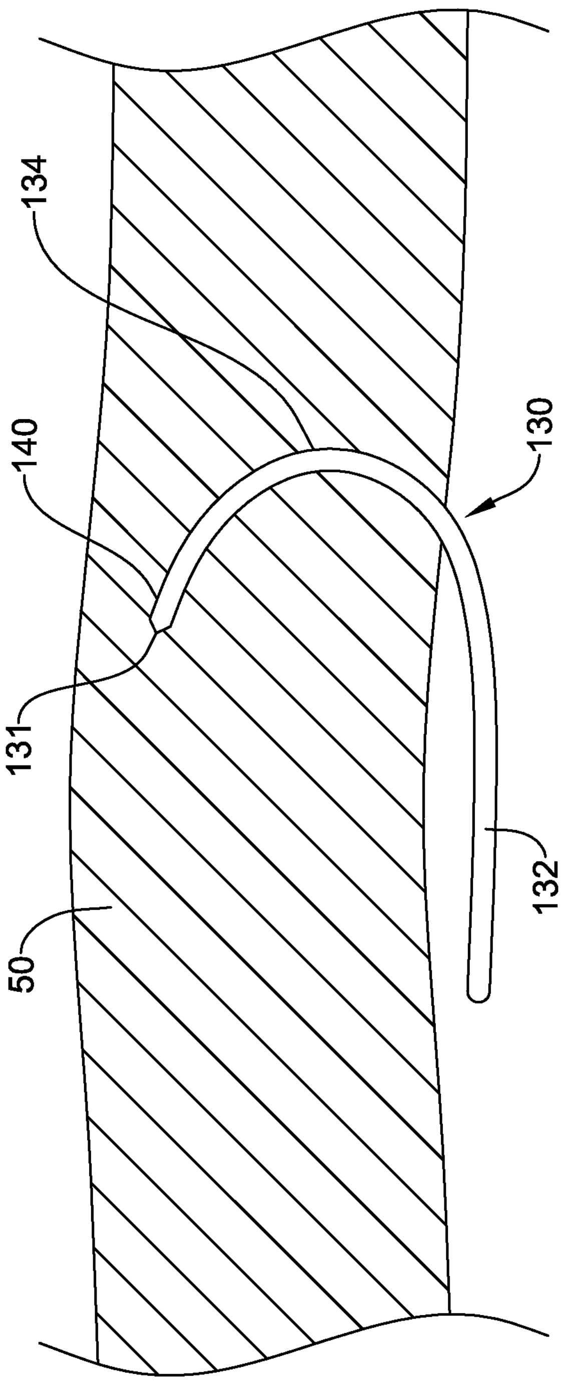
FIG. 4 Prior Art
FIG. 4 illustrates penetration of a prior art anchor member into tissue.

In some embodiments, the expandable framework 110 may include a plurality of anchor members 130 extending radially outward from the plurality of interconnected struts in the expanded configuration. In some embodiments, at least some of the plurality of anchor members 130 extend through the occlusive element 120. Some additional details of the plurality of anchor members 130 are shown in FIG. 4. In some embodiments, each anchor member of the plurality of anchor members 130 includes a base portion 132 fixedly attached to the plurality of interconnected struts, an anchor tip portion 140, and a curved portion 134 extending from the base portion 132 to the anchor tip portion 140.

As also shown in FIG. 4, in some previous configurations of the medical implant 100, the plurality of anchor members 130 include a distal tip 131 configured to pierce and extend into tissue 50 (e.g., a wall) of the left atrial appendage in the expanded configuration. In some previous configurations, the plurality of anchor members 130 is formed from a wire or similar material. In some embodiments, the ability to form shapes and varying configurations of the plurality of anchor members 130 may be limited by the material(s) used and/or the configuration of the medical implant 100. In some patients and/or anatomies, the structural arrangement of the left atrial appendage and/or the thickness of the tissue 50 may leave the plurality of anchor members 130 (and/or the distal tip 131 thereof) at risk of overpenetration and/or perforation of the tissue 50 (e.g. pericardial effusion). The circumstances causing this risk may not be easily seen or identified ahead of time. As such, new configurations for the plurality of anchor members 130 and/or the anchor tip portion 140 of the plurality of anchor members 130 disclosed herein may offer new and/or improved benefits for patient safety and/or effectiveness of the medical implant 100.

In some embodiments, the anchor tip portion 140 of the plurality of anchor members 130 may include a central penetrating element 142, at least one tissue support element 150 extending outward from the central penetrating element

Figure 5:
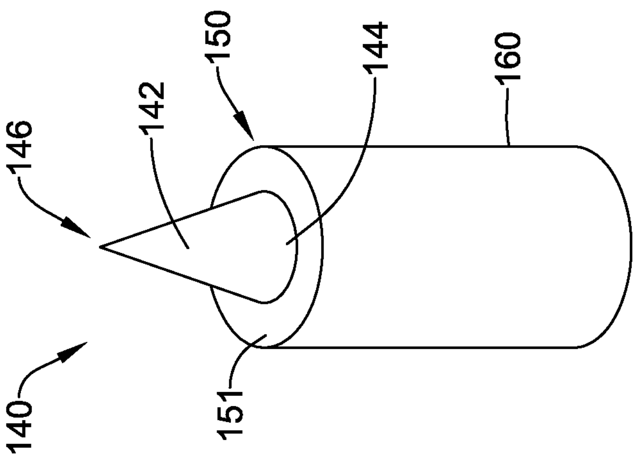
FIG. 5 illustrates selected aspects of an anchor member according to the disclosure.

142, and a shaft portion 160 extending opposite the central penetrating element 142, as seen in FIG. 5. In at least some embodiments, the shaft portion 160 may be configured to engage with the curved portion 134 of the plurality of anchor members 130. In some embodiments, the shaft portion 160 may be integrally formed with the curved portion 134. In some embodiments, the shaft portion 160 may be fixedly attached to the curved portion 134. Other configurations are also contemplated.

In some embodiments, the central penetrating element 142 may be configured to penetrate into tissue and/or the wall of the left atrial appendage. The at least one tissue support element 150 may be configured to engage tissue and/or the wall of the left atrial appendage. In at least some embodiments, the at least one tissue support element 150 may extend radially outward from the central penetrating element 142. In some embodiments, the at least one tissue support element 150 may be disposed symmetrically about a central axis of the central penetrating element 142. In some embodiments, the at least one tissue support element 150 may extend circumferentially about the central axis of the central penetrating element 142. In some embodiments, the at least one tissue support element 150 may extend circumferentially around the central penetrating element 142. In some embodiments, the at least one tissue support element 150 may be symmetric about the central penetrating element 142.

In some embodiments, the anchor tip portion 140 may be devoid of any element or structure configured to penetrate into tissue and/or the wall of the left atrial appendage other than the central penetrating element 142. For example, all other structure, elements, and/or features of the anchor tip portion 140 may be expressly designed, adapted, and/or configured to avoid penetrating into tissue and/or the wall of the left atrial appendage. In at least some embodiments, the at least one tissue support element 150 may be configured to prevent the central penetrating element 142 from penetrating completely through the wall of the left atrial appendage.

In some embodiments, the anchor tip portion 140 may extend in a first direction from the curved portion 134. In some embodiments, the central penetrating element 142 extends in the first direction along the central axis from a root 144 to a free end 146. In at least some embodiments, the central penetrating element 142 has a first radial extent from the central axis at the root 144 and a second radial extent from the central axis at the free end 146, wherein the first radial extent is greater than the second radial extent. In some embodiments, the central penetrating element 142 has a generally conical shape. Other configurations, including combinations thereof, are also contemplated.

In some embodiments, the at least one tissue support element 150 may be integrally formed with the central penetrating element 142. In some embodiments, the at least one tissue support element 150 may be monolithically formed with the central penetrating element 142. In some embodiments, the at least one tissue support element 150 may be integrally formed with the central penetrating element 142 as a single monolithic structure. In some alternative configurations, the at least one tissue support element 150 and the central penetrating element 142 may be formed independently and/or separately from each and later assembled together to form the anchor tip portion 140. Other configurations, including combinations thereof, are al so contemplated.

In some embodiments, the anchor tip portion 140, the central penetrating element 142, and/or the at least one tissue support element 150 may be laser cut from a tubular structure. In some embodiments, the anchor tip portion 140, the central penetrating element 142, and/or the at least one tissue support element 150 may be laser cut from the same tubular structure as the expandable framework 110 and/or the plurality of interconnected struts. In some embodiments, the anchor tip portion 140, the central penetrating element 142, and/or the at least one tissue support element 150 may be formed from a wire, a rod, or other round stock. In some embodiments, the anchor tip portion 140, the central penetrating element 142, and/or the at least one tissue support element 150 may be machined, turned on a lathe, cut with a waterjet, formed by chemical dissolution, formed using electro discharge machining (EDM), injection molded, cast, or other suitable manufacturing means. Other configurations, including combinations thereof, are also contemplated.

In some embodiments, the anchor tip portion 140, the central penetrating element 142, and/or the at least one tissue support element 150 may have a generally polygonal cross-section (e.g., square, rectangular, hexagonal, etc.). In some embodiments, the anchor tip portion 140, the central penetrating element 142, and/or the at least one tissue support element 150 may have a generally round and/or circular cross-section. Other configurations, including combinations thereof, are also contemplated.

In some embodiments, the at least one tissue support element 150 may have different configurations. In some embodiments, the at least one tissue support element 150 may include a substantially planar surface 151 extending outward from the central penetrating element 142, as seen in FIG. 5 for example. In some embodiments, the shaft portion 160 may have a radial extent that is equal to and/or very similar to a radial extent of the at least one tissue support element 150.

Figure 7:
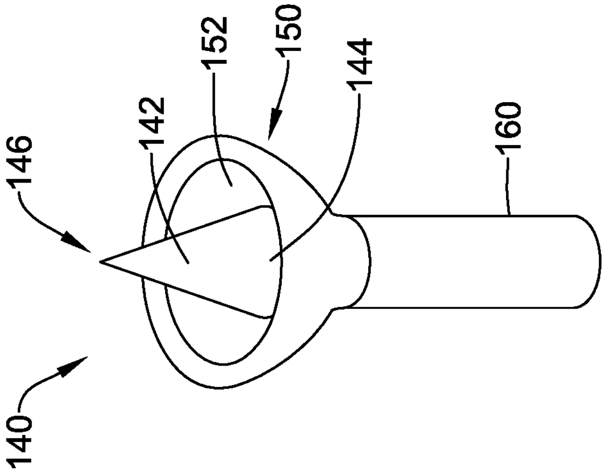
FIG. 7 illustrates selected aspects of an anchor member according to the disclosure.
Figure 6:
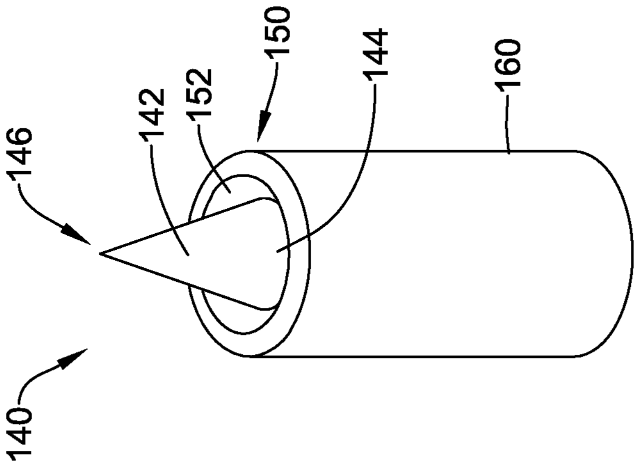
FIG. 6 illustrates selected aspects of an anchor member according to the disclosure.

In some embodiments, the at least one tissue support element 150 may extend outward and in the first direction from an intersection of the at least one tissue support element 150 and the central penetrating element 142, as seen in FIGS. 6-7 for example. In some embodiments, the at least one tissue support element 150 may extend radially outward and in the first direction away from the root 144 of the central penetrating element 142. In some embodiments, the at least one tissue support element 150 may be concave and/or may include a concave portion 152 opening toward the free end 146 of the central penetrating element 142. In some embodiments, the central penetrating element 142 may extend in the first direction from inside the at least one tissue support element 150 and/or the concave portion 152 of the at least one tissue support element 150. In some embodiments, the root 144 of the central penetrating element 142 may be disposed within the at least one tissue support element 150 and/or the concave portion 152 of the at least one tissue support element 150. In some embodiments, the shaft portion 160 may have a radial extent less than the radial extent of the at least one tissue support element 150. In some embodiments, the shaft portion 160 have a radial extent that is at least 20% less than the radial extent of the at least one tissue support element 150. In some embodiments, the shaft portion 160 have a radial extent that is at least 30% less than the radial extent of the at least one tissue support element 150. In some embodiments, the shaft portion 160 have a radial extent that is at least 40% less than the radial extent of the at least one tissue support element 150. In some embodiments, the shaft portion 160 have a radial extent that is at least 50% less than the radial extent of the at least one tissue support element 150. In some embodiments, the shaft portion 160 have a radial extent that is at least 60% less than the radial extent of the at least one tissue support element 150. In some embodiments, the shaft portion 160 have a radial extent that is at least 70% less than the radial extent of the at least one tissue support element 150. Other configurations are also contemplated.

Figure 8:
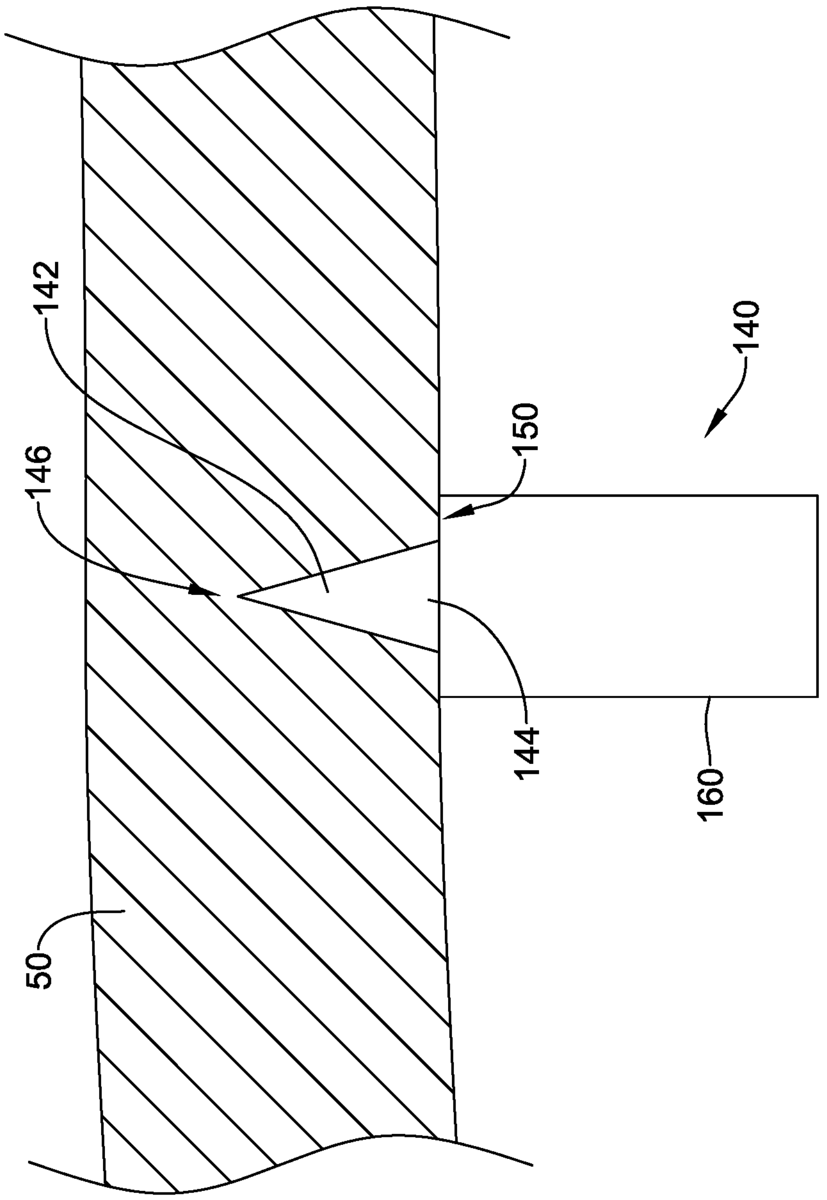
FIG. 8 illustrates engagement of the anchor member of FIG. 5 with tissue.
Figure 12:
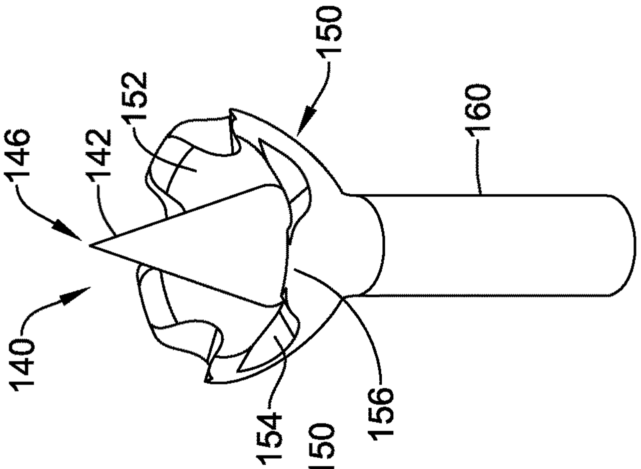
FIG. 12 illustrates selected aspects of an anchor member according to the disclosure.
Figure 11:
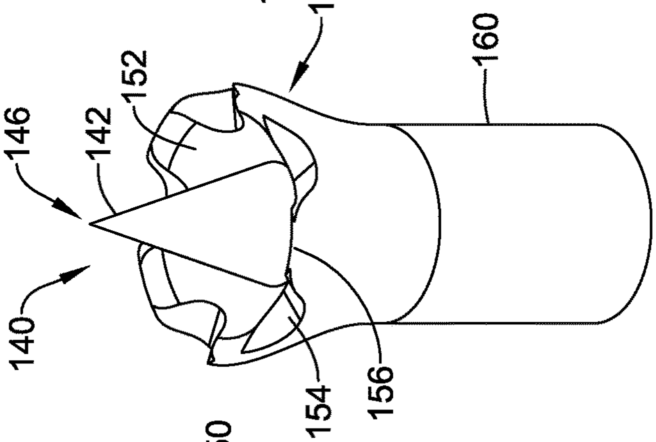
FIG. 11 illustrates selected aspects of an anchor member according to the disclosure.
Figure 10:
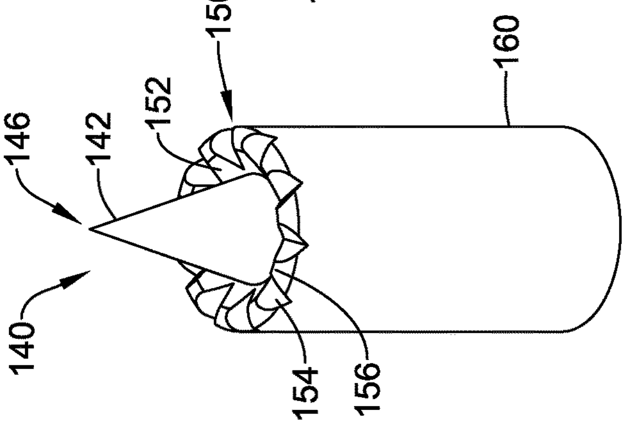
FIG. 10 illustrates selected aspects of an anchor member according to the disclosure.
Figure 9:
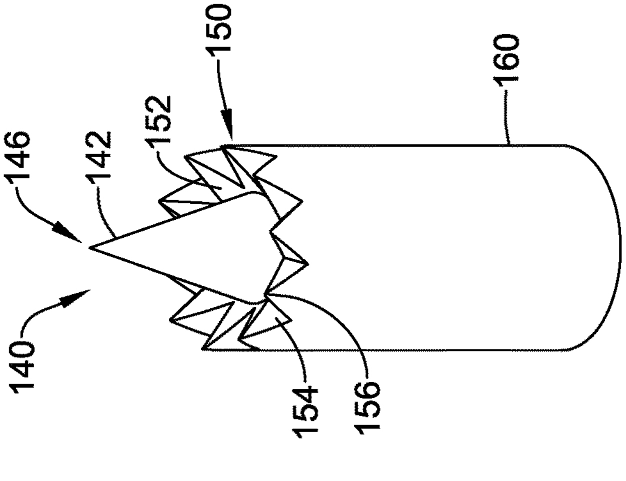
FIG. 9 illustrates selected aspects of an anchor member according to the disclosure.
Figure 14:
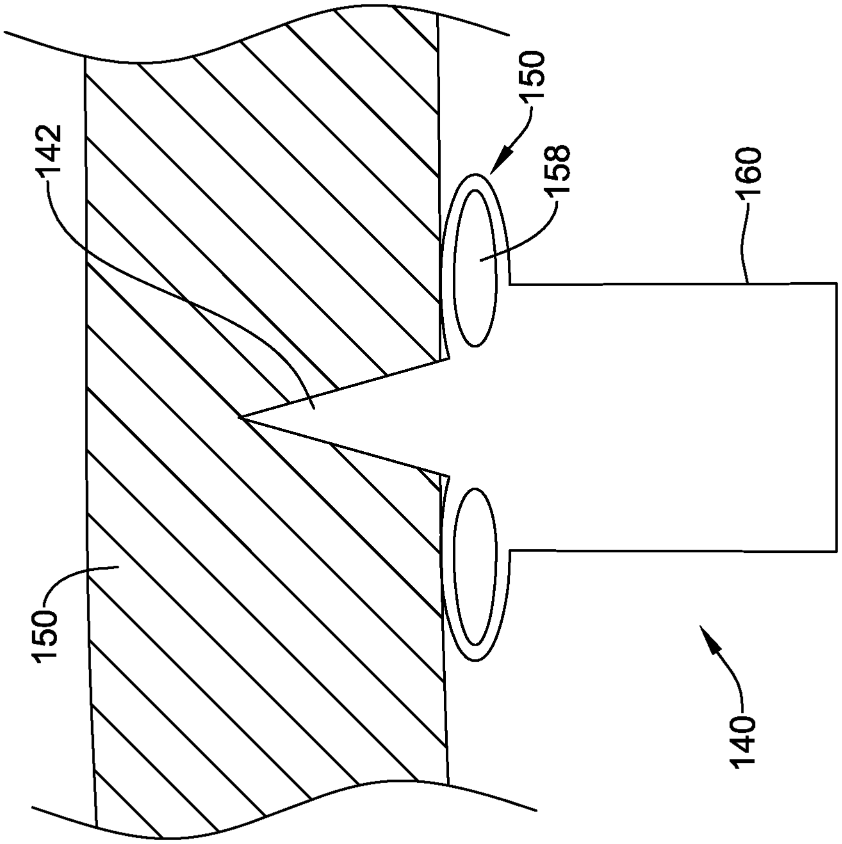
FIG. 14 illustrates engagement of the anchor member of FIG. 13 with tissue.

FIG. 8 schematically shows engagement of the anchor tip portion 140 of the plurality of anchor members 130 with the tissue 50. For illustrative purposes only, FIG. 8 shows the anchor tip portion 140 of FIG. 5 engaged with the tissue 50. It shall be understood that other embodiments of the anchor tip portion 140 may act and/or function in a similar manner, unless expressly stated otherwise. As discussed herein, the central penetrating element 142 may be configured to penetrate into the tissue 50 and/or the wall of the left atrial appendage. The at least one tissue support element 150 may be configured to engage the tissue 50 and/or the wall of the left atrial appendage. In some embodiments, the at least one tissue support element 150 may be configured to function as a stop limiting further penetration of the central penetrating element 142 into the tissue 50 and/or the wall of the left atrial appendage. In some embodiments, all other structure, elements, and/or features of the anchor tip portion 140 may be expressly designed, adapted, and/or configured to avoid penetrating into the tissue 50 and/or the wall of the left atrial appendage. In at least some embodiments, the at least one tissue support element 150 may be configured to prevent the central penetrating element 142 from penetrating completely through the tissue 50 and/or the wall of the left atrial appendage.

FIGS. 9-12 illustrate additional example configurations for the anchor tip portion 140. In some embodiments, the at least one tissue support element 150 may include a plurality of notches 154 formed around a perimeter of the concave portion 152 of the at least one tissue support element 150. In some embodiments, the plurality of notches 154 may extend circumferentially around the concave portion 152 of the at least one tissue support element 150. In some embodiments, the plurality of notches 154 may open in the first direction and/or toward the free end 146 of the central penetrating element 142. In some embodiments, the plurality of notches 154 may form and/or define a plurality of ridges 156. In some embodiments, the plurality of notches 154 and/or the plurality of ridges 156 may alternate around the circumference and/or the perimeter of the concave portion 152.

In some embodiments, the plurality of notches 154 and/or the plurality of ridges 156 may be configured to engage tissue and/or the wall of the left atrial appendage. In some embodiments, the plurality of notches 154 and/or the plurality of ridges 156 may improve stability of the anchor tip portion 140 when engaged with tissue and/or the wall of the left atrial appendage. In some embodiments, the plurality of notches 154 and/or the plurality of ridges 156 may create and/or may be configured to create mild inflammation of the tissue and/or the wall of the left atrial appendage to promote better tissue growth around the anchor tip portion 140, thereby further improving anchoring of the medical implant 100 within the left atrial appendage.

FIGS. 13-19 illustrate selected aspects of some additional configurations for the anchor tip portion 140. In some embodiments, the anchor tip portion 140 may be formed as a two-dimensional structure. For example, as discussed herein, the anchor tip portion 140, the central penetrating element 142, and/or the at least one tissue support element 150 may be laser cut from a tubular structure and/or from a piece of flat material, as shown schematically in FIG. 13. In some embodiments, the at least one tissue support element 150 may be configured to shift radially outward from the central penetrating element 142 as the at least one tissue support element 150 engages the tissue 50 and/or the wall of the left atrial appendage, as shown schematically in FIG. 14. In some embodiments, the at least one tissue support element 150 may include a hollow interior space 158. In some embodiments, the at least one tissue support element 150 may be integrally formed with the anchor tip portion 140, the shaft portion 160, and/or the central penetrating element 142 as a single monolithic structure.

Figure 13:
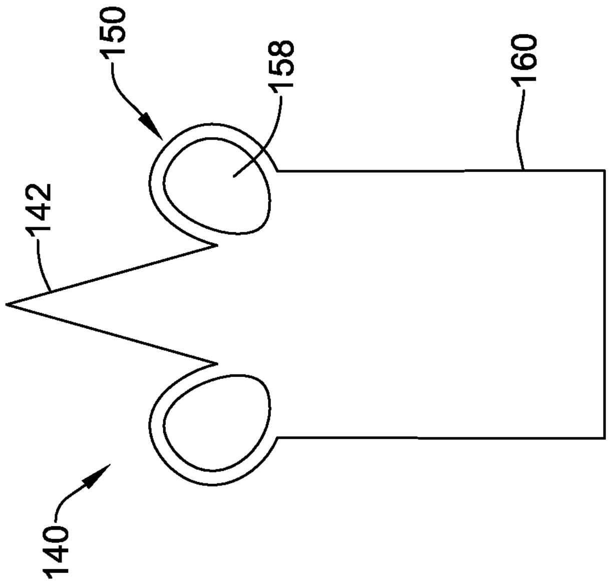
FIG. 13 illustrates selected aspects of an anchor member according to the disclosure.

In some embodiments, the at least one tissue support element 150 may include two tissue support elements, as seen in FIG. 13. In some embodiments, the at least one tissue support element 150 may be spaced apart circumferentially around the central axis of the central penetrating element 142 and/or may be spaced apart circumferentially around the central penetrating element 142. In some embodiments, the at least one tissue support element 150 may be equally spaced apart circumferentially around the central axis of the central penetrating element 142 and/or may be equally spaced apart circumferentially around the central penetrating element 142. In some embodiments, the at least one tissue support element 150 may include two tissue support elements disposed opposite each other relative to the central axis of the central penetrating element 142 and/or relative to the central penetrating element 142. In some embodiments, the two tissue support elements may be disposed about 180 degrees apart from each other about the central axis and/or the central penetrating element 142. In some embodiments, positioning the two tissue support elements this way may facilitate formation, fabrication, and/or machining of the hollow interior space 158. Other configurations are also contemplated.

Figure 15:
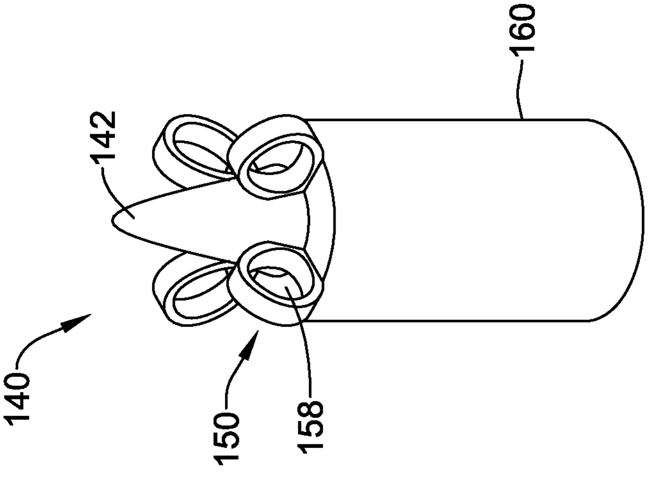
FIG. 15 illustrates selected aspects of an anchor member according to the disclosure.

In some embodiments, the at least one tissue support element 150 may include four tissue support elements, as seen in FIG. 15. In some embodiments, the at least one tissue support element 150 may be spaced apart circumferentially around the central axis of the central penetrating element 142 and/or may be spaced apart circumferentially around the central penetrating element 142. In some embodiments, the at least one tissue support element 150 may be equally spaced apart circumferentially around the central axis of the central penetrating element 142 and/or may be equally spaced apart circumferentially around the central penetrating element 142. In some embodiments, the four tissue support elements may be disposed about 90 degrees apart from each other about the central axis and/or the central penetrating element 142. In some embodiments, positioning the four tissue support elements this way may facilitate formation, fabrication, and/or machining of the hollow interior space 158. Other configurations are also contemplated.

Figure 17:
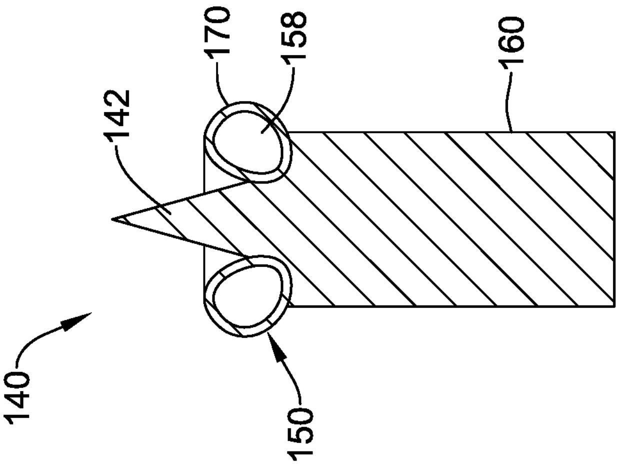
FIG. 17 is a cross-sectional view of the anchor member of FIG. 16.
Figure 16:
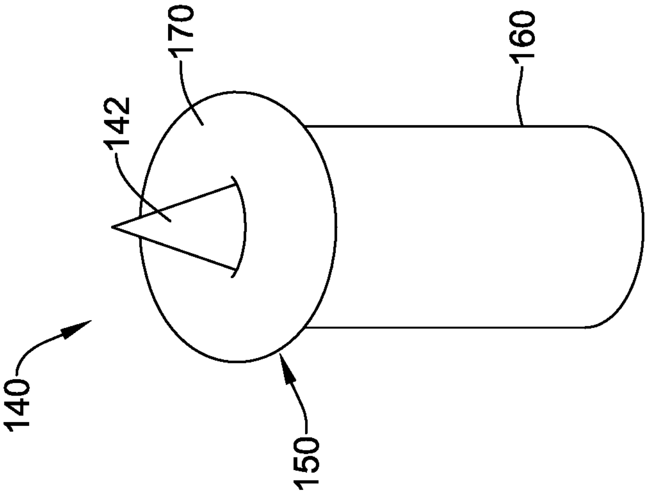
FIG. 16 illustrates selected aspects of an anchor member according to the disclosure.

In some embodiments, the at least one tissue support element 150 may include an annular ring 170 extending circumferentially around the central axis and/or the central penetrating element 142, as seen in FIG. 16. In some embodiments, the annular ring 170 may be integrally formed with the anchor tip portion 140, the shaft portion 160, and/or the central penetrating element 142 as a single monolithic structure. In some embodiments, the annular ring 170 may be formed as a separate element, as seen in FIG. 17, and fixedly attached, bonded, welded, etc. to the anchor tip portion 140, the central penetrating element 142, and/or the shaft portion 160. In some embodiments, the shaft portion 160 and/or the central penetrating element 142 may be formed from a metallic material and the annular ring 170 may be formed from a polymeric material. The annular ring 170 may include the hollow interior space 158 disposed therein and may function in a manner similar to the at least one tissue support element 150 shown and/or described with respect to FIGS. 13-15. Other configurations and materials, including combinations thereof, are also contemplated.

Figure 19:
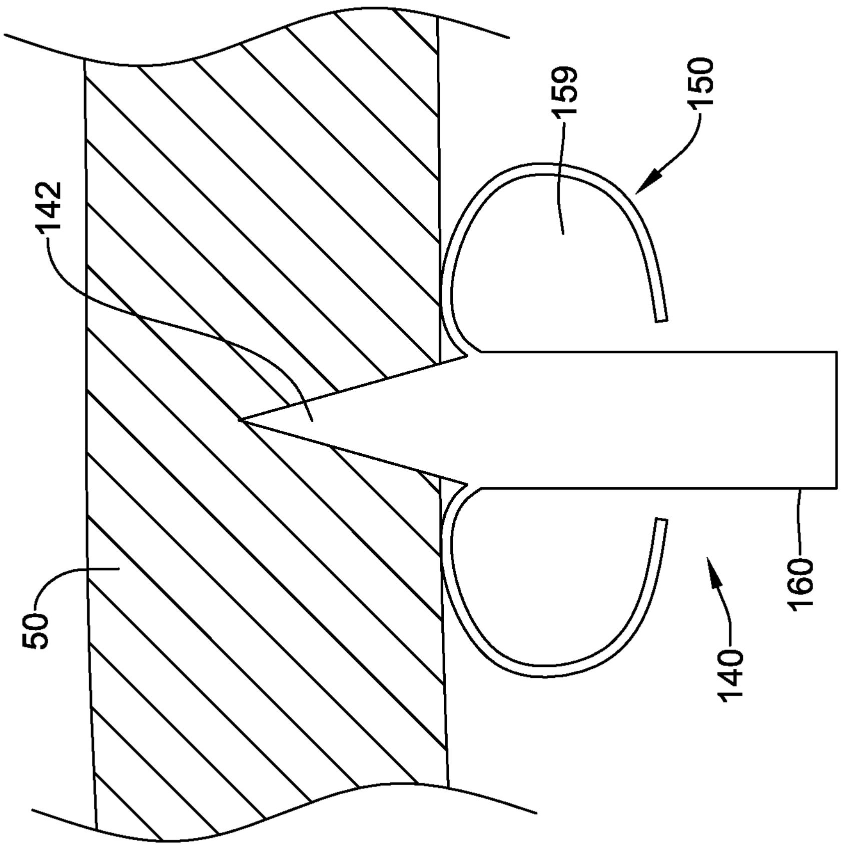
FIG. 19 illustrates engagement of the anchor member of FIG. 18 with tissue.
Figure 18:
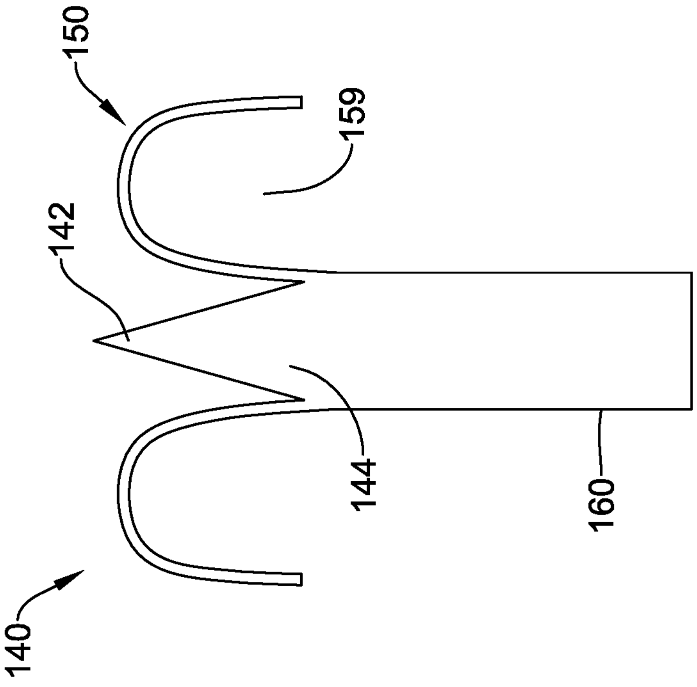
FIG. 18 illustrates selected aspects of an anchor member according to the disclosure.

In some embodiments, the at least one tissue support element 150 may be and/or include an open-ended loop 180, as seen in FIGS. 18-19. In at least some embodiments, the at least one tissue support element 150 may be disposed and/or fixedly attached to the central penetrating element 142 and/or the shaft portion 160 at and/or proximate the root 144 of the central penetrating element 142. In some embodiments, the at least one tissue support element 150 may be and/or may include more than one open-ended loop. In some embodiments, the at least one tissue support element 150 may be and/or may include two open-ended loops (e.g., similar to FIG. 13), four open-ended loops (e.g., similar to FIG. 15), or another quantity of open-ended loops. In some embodiments, the at least one tissue support element 150, the open-ended loop 180, and/or the more than one open-ended loop may be symmetric and/or may be disposed symmetrically about the central penetrating element 142.

In some embodiments, the at least one tissue support element 150 may be spaced apart circumferentially around the central axis of the central penetrating element 142 and/or may be spaced apart circumferentially around the central penetrating element 142. In some embodiments, the at least one tissue support element 150 may be equally spaced apart circumferentially around the central axis of the central penetrating element 142 and/or may be equally spaced apart circumferentially around the central penetrating element 142.

In some embodiments, the open-ended loop 180 may extend continuously around the central axis of the central penetrating element 142 and/or may extend continuously around the circumference of the central penetrating element 142 (e.g., similar to FIGS. 16-17). Similar to at least some other embodiments, the at least one tissue support element 150 may include a hollow interior space 159, but the hollow interior space 159 of FIGS. 18-19 may be open-ended and/or may not be completely enclosed.

In some embodiments, the at least one tissue support element 150 may be configured to shift radially outward from the central penetrating element 142 as the at least one tissue support element 150 engages the tissue 50 and/or the wall of the left atrial appendage, as shown schematically in FIG. 19. In some embodiments, the at least one tissue support element 150 may be integrally formed with the anchor tip portion 140, the shaft portion 160, and/or the central penetrating element 142 as a single monolithic structure. In some alternative configurations, the at least one tissue support element 150 may be made and/or constructed separately from the anchor tip portion 140 and/or the central penetrating element 142 and later fixedly attached thereto. Other configurations are also contemplated.

Figure 21:
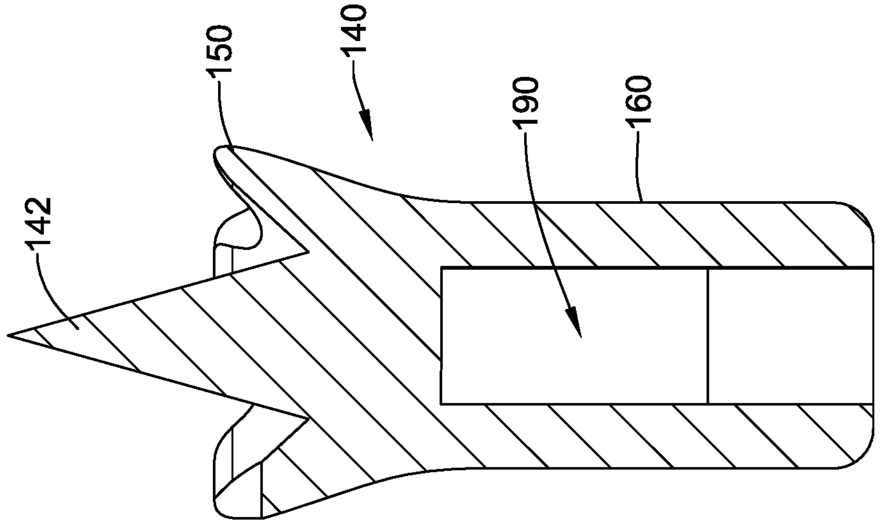
FIG. 21 is a cross-sectional view of the anchor member of FIG. 20.
Figure 20:
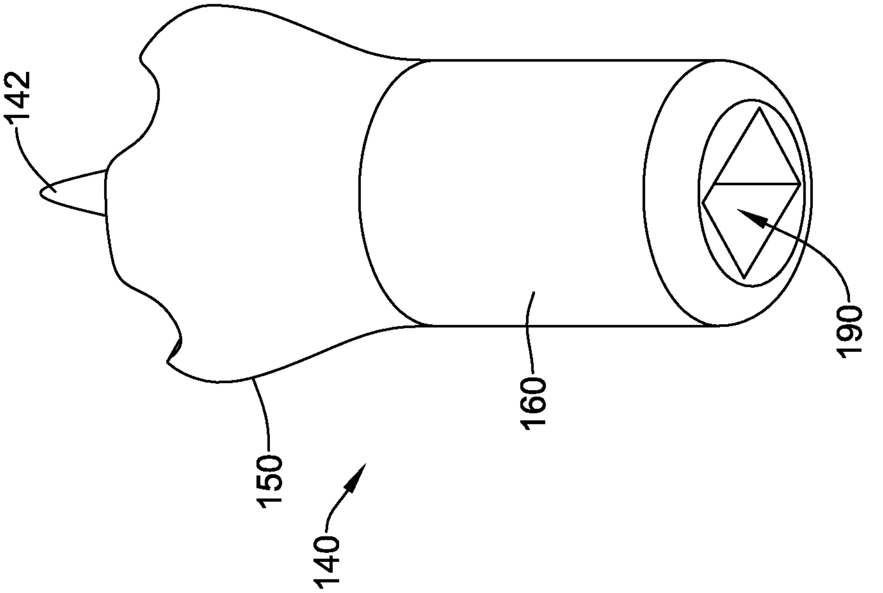
FIG. 20 illustrates selected aspects of an anchor member according to the disclosure.

FIGS. 20-21 illustrates selected aspects and/or features of the anchor tip portion 140 that may be applied to and/or may be included in any and/or all embodiments described herein. While these aspects and/or features are shown with respect to the anchor tip portion 140 of FIG. 11, it shall be understood that the aspects and/or features shown are not limited to the anchor tip portion 140 of FIG. 11.

Figure 22:
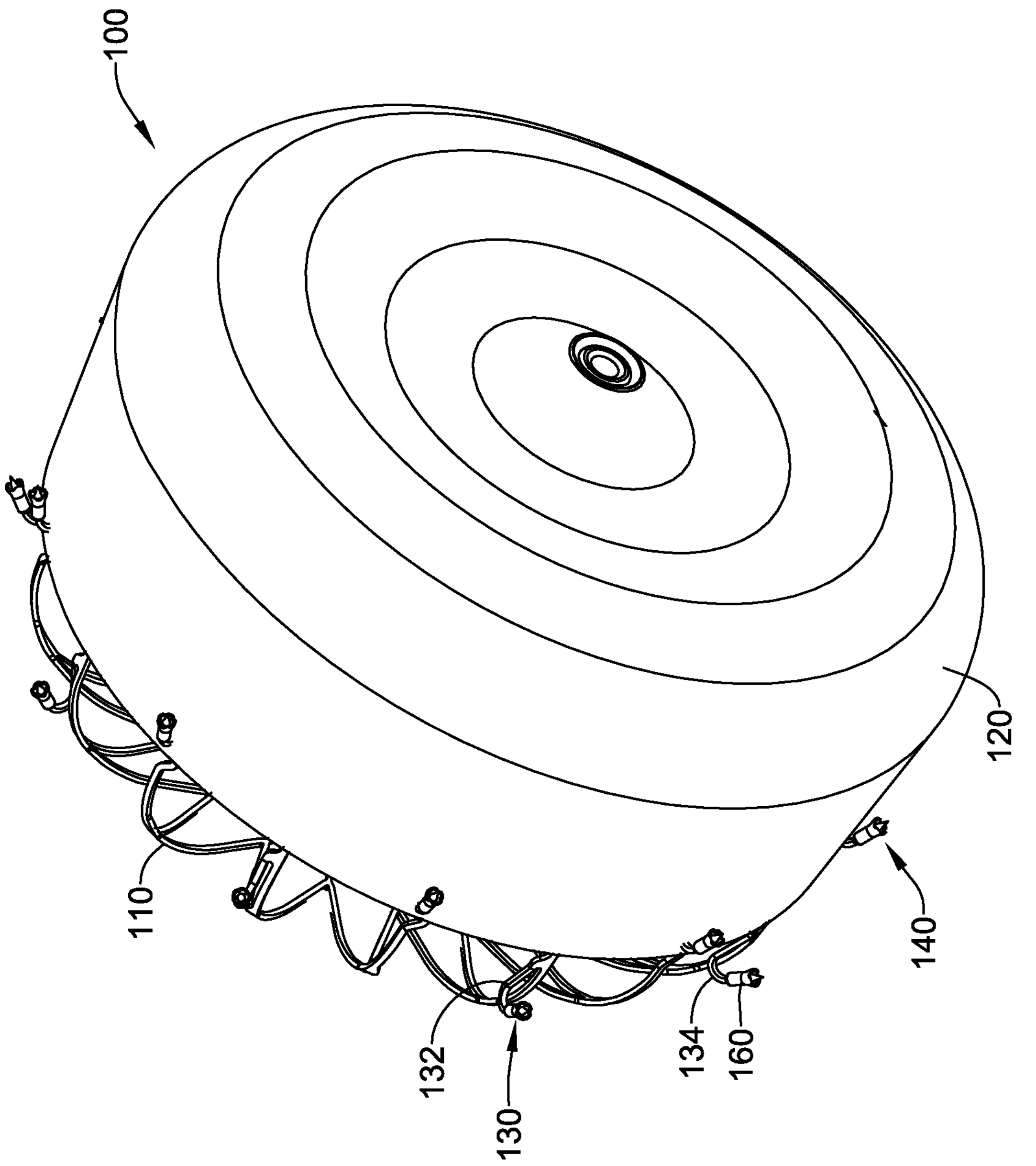
FIG. 22 illustrates selected aspects of a medical implant having a plurality of anchor members according to the disclosure.

In some embodiments, the anchor tip portion 140 may include a proximal cavity 190 formed within the shaft portion 160 of the anchor tip portion 140. In some embodiments, the proximal cavity 190 may be sized, shaped, configured, and/or adapted to receive at least a portion of one of the plurality of anchor members 130 (e.g., the curved portion 134, an extension of the curved portion 134, etc.). In some embodiments, the proximal cavity 190 may be configured to engage with the curved portion 134 of the plurality of anchor members 130 and/or an extension of the curved portion 134, as seen in FIG. 22. In some embodiments, the shaft portion 160 may be fixedly attached to the curved portion 134. In some embodiments, an adhesive material and/or a bonding agent may be disposed within the proximal cavity 190. In some embodiments, the curved portion 134 and/or the extension of the curved portion 134 may be mechanically attached and/or interlocked to the shaft portion 160, such as with a cross pin, a spring element, a spring-loaded feature, a spring-biased feature, or other interlocking element. In some embodiments, the anchor tip portion 140 and/or the shaft portion 160 may be welded, brazed, soldered, etc. onto the curved portion 134 and/or the extension of the curved portion 134. In some embodiments, the anchor tip portion 140 and/or the shaft portion 160 may be overmolded onto the curved portion 134 and/or the extension of the curved portion 134. Other configurations, including combinations thereof, are also contemplated.

Figure 24:
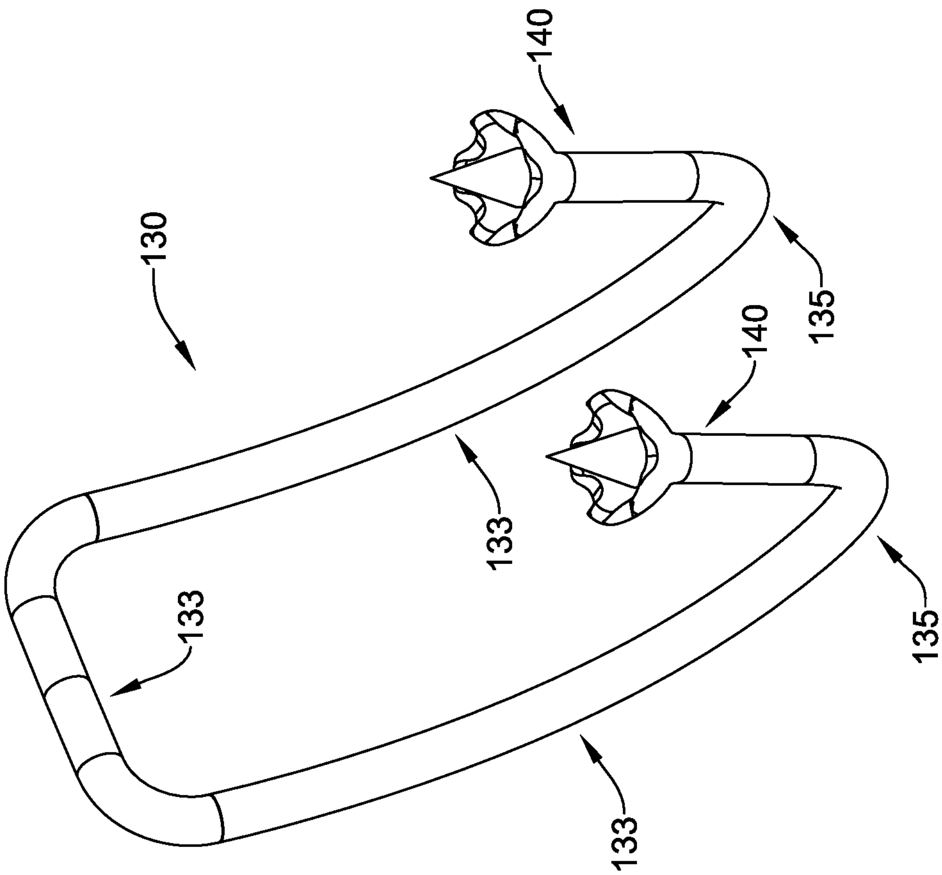
FIG. 24 illustrates selected aspects of an anchor member according to the disclosure.
Figure 23:
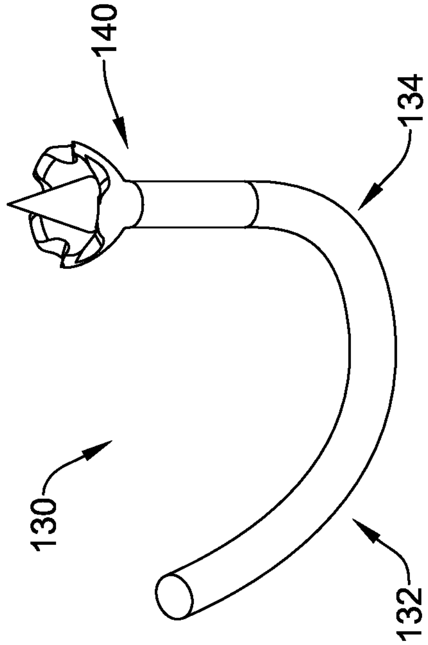
FIG. 23 illustrates selected aspects of an anchor member according to the disclosure.

In some alternative embodiments, the plurality of anchor members 130 and/or the anchor tip portion 140 thereof may be formed and/or assembled separately from the medical implant 100 and/or the expandable framework 110, and later fixedly attached thereto. FIG. 23 illustrates one example configuration of an anchor member having a single anchor tip portion, wherein the anchor member may be fixedly attached to the expandable framework 110 during manufacturing and/or assembly of the medical implant 100. In some embodiments, the anchor member of FIG. 24 may be formed from a single wire or a single shaft member that forms the base portion 132 and the curved portion 134. FIG. 24 illustrates one example configuration of an anchor member having dual anchor tip portions, wherein the anchor member may be fixedly attached to the expandable framework 110 during manufacturing and/or assembly of the medical implant 100. In some embodiments, the anchor member of FIG. 24 may be formed from a single wire or a single shaft member that forms a U-shaped base portion 133 and dual curved portions 135. In some embodiments, the anchor member of FIG. 24 may be formed from multiple individual anchor members (e.g., FIG. 23) that are fixedly attached to each other before being fixedly attached to the expandable framework 110.

Figure 25:
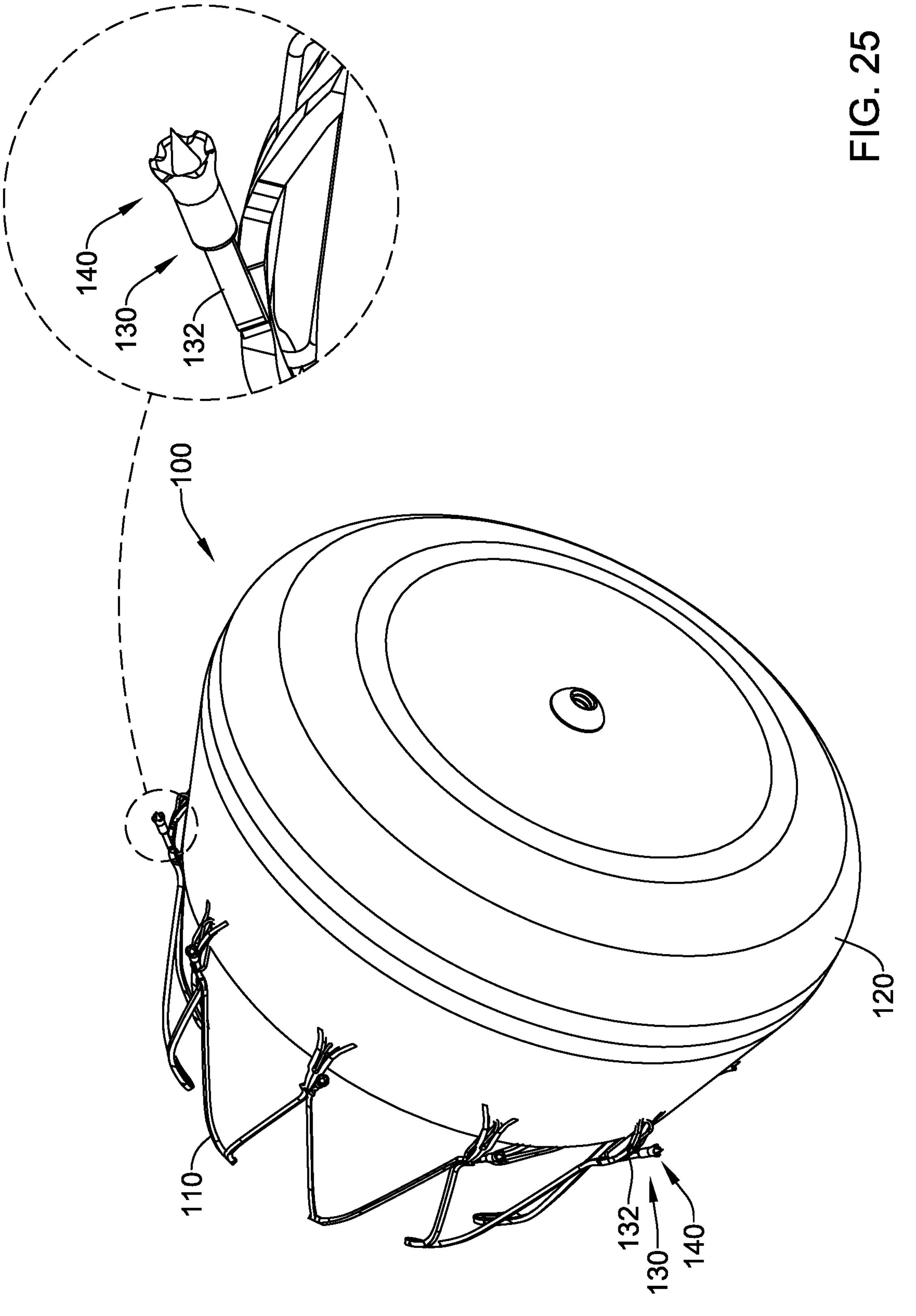
FIG. 25 illustrates selected aspects of a medical implant having a plurality of anchor members according to the disclosure.

Referring back briefly to FIGS. 20-22, in some alternative embodiments, the proximal cavity 190 may be configured to engage with the plurality of anchor members 130 and/or the base portion 132, as seen in FIG. 25. In some embodiments, the plurality of anchor members 130 may be devoid of the curved portion 134. In some embodiments, the shaft portion 160 may be fixedly attached to the base portion 132. In some embodiments, an adhesive material and/or a bonding agent may be disposed within the proximal cavity 190. In some embodiments, the base portion 132 may be mechanically attached and/or interlocked to the shaft portion 160, such as with a cross pin, a spring element, a spring-loaded feature, a spring-biased feature, or other interlocking element. In some embodiments, the anchor tip portion 140 and/or the shaft portion 160 may be welded, brazed, soldered, etc. onto the base portion 132. In some embodiments, the anchor tip portion 140 and/or the shaft portion 160 may be overmolded onto the base portion 132. Other configurations, including combinations thereof, are also contemplated.

In some embodiments, a method of manufacturing the medical implant 100 may include forming and/or cutting the expandable framework 110 from a unitary tubular member in the collapsed configuration. Alternatively, the method of manufacturing the medical implant 100 may include forming and/or cutting the expandable framework 110 from a flat sheet of material that is later rolled and/or formed into a tubular member. After forming the flat sheet of material into a tubular member, the tubular member may be welded or otherwise fixedly secured into a tubular shape. In some embodiments, forming and/or cutting the expandable framework 110 may be done via laser, waterjet, machining, etc. Other manufacturing methods and/or processes are also contemplated.

After forming and/or cutting the expandable framework 110, the method may include forming the expandable framework 110 into the expanded configuration. As part of forming the expandable framework 110 into the expanded configuration, the method may include bending each anchor member of the plurality of anchor members 130. In some embodiments, each anchor member may be bent individually. In some embodiments, two or more anchor members may be bent together as a group. In some embodiments, after forming the expandable framework 110 into the expanded configuration, the method may include heat setting the expandable framework 110 and/or the plurality of anchor members 130 in the expanded configuration. Other configurations and/or orders of operations are also contemplated.

In some embodiments, the method of manufacturing the medical implant 100 may include securing the occlusive element 120 to the expandable framework 110. In some embodiments, at least some of the plurality of anchor members 130 may extend through the occlusive element 120 in the expanded configuration. In some embodiments, the occlusive element 120 may be disposed on, along, and/or over an exterior surface of the expandable framework 110. Other configurations are also contemplated.

In some embodiments, the method of manufacturing the medical implant 100 may include fixedly attaching the anchor tip portion 140 to the plurality of anchor members 130, as discussed herein. In some embodiments, forming and/or cutting the expandable framework 110 may include forming and/or cutting the plurality of anchor members 130 and/or the anchor tip portion 140 thereof. Other configurations are also contemplated.

The materials that can be used for the various components of the medical implants, systems, and methods of manufacturing disclosed herein may include those commonly associated with medical devices. For simplicity purposes, the following discussion refers to the system. However, this is not intended to limit the system, devices, and/or methods described herein, as the discussion may be applied to other elements, members, components, or devices disclosed herein, such as, but not limited to, the expandable framework, the plurality of interconnected struts, the plurality of anchor members, the occlusive element, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN®), polyether block ester, polyurethane, polypropylene (PP), polyvinylchloride (PVC), polyether-ester (for example, ARNITEL®), ether or ester based copolymers (for example, butylene/poly(alkylene ether) phthalate and/or other polyester elastomers such as HYTREL®), polyamide (for example, DURETHAN® or CRISTAMID®), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID®), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® or ChronoSil®), biocompatible polymers, other suitable materials, or mixtures, combinations, copolymers thereof, polymer/metal composites, and the like. In some embodiments, the system and/or components thereof can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, portions or all of the system and/or components thereof may be doped with, made of, or otherwise include a radiopaque material. Radiopaque materials are understood to be materials capable of producing a relatively bright image on a fluoroscopy screen or another imaging technique (e.g., ultrasound, etc.) during a medical procedure. This relatively bright image aids a user in determining the location of the system. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MM) compatibility is imparted into the system. For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the system may include a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. In some embodiments, the yarns may be made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible system.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-protein and/or anti-bacterial agents (such as 2-methacryroyloxyethyl phosphorylcholine (MPC) and its polymers or copolymers); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); immunosuppressants (such as the "olimus" family of drugs, rapamycin analogues, macrolide antibiotics, biolimus, everolimus, zotarolimus, temsirolimus, picrolimus, novolimus, myolimus, tacrolimus, sirolimus, pimecrolimus, etc.); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical implant for occluding a left atrial appendage, comprising:

an expandable framework configured to shift between a collapsed configuration and an expanded configuration;

wherein the expandable framework includes a plurality of interconnected struts and a plurality of anchor members extending radially outward from the plurality of interconnected struts in the expanded configuration;

wherein each anchor member of the plurality of anchor members includes a base portion fixedly attached to the plurality of interconnected struts and an anchor tip portion;

wherein the anchor tip portion includes a central penetrating element extending in a first direction and a concave tissue support element that extends circumferentially all of the way around and radially outward from the central penetrating element, wherein the concave tissue support element has an upper surface facing the first direction, the upper surface having a plurality of notches formed therein, wherein the plurality of notches are spaced apart around a circumference of the concave tissue support element;

wherein the concave tissue support element is configured to be non-penetrating.

2. The medical implant of claim 1, wherein the concave tissue support element is disposed symmetrically about a central axis of the central penetrating element.

3. The medical implant of claim 2, wherein the concave tissue support element extends circumferentially about the central axis of the central penetrating element.

4. The medical implant of claim 1, wherein the concave tissue support element is configured to shift radially outward from the central penetrating element as the at least one concave tissue support element engages tissue.

5. The medical implant of claim 4, wherein the concave tissue support element includes a hollow interior space.

6. The medical implant of claim 1, wherein the anchor tip portion extends in the first direction from a curved portion of each anchor member, the curved portion extending from the base portion to the anchor tip portion.

7. The medical implant of claim 6, wherein the central penetrating element extends in the first direction to a free end.

8. The medical implant of claim 7, wherein the concave tissue support element extends outward and in the first direction from an intersection of the concave tissue support element and the central penetrating element.

9. The medical implant of claim 8, wherein the central penetrating element extends in the first direction from inside the concave tissue support element.

10. The medical implant of claim 1, wherein the concave tissue support element is monolithically formed with the central penetrating element.

11. The medical implant of claim 1, wherein the central penetrating element has a generally conical shape.

12. A medical device system, comprising:

a catheter;

a core wire movably disposed within a lumen of the catheter; and a medical implant for occluding a left atrial appendage releasably connected to a distal portion of the core wire;

wherein the medical implant includes an expandable framework configured to shift between a collapsed configuration and an expanded configuration;

wherein the expandable framework includes a plurality of interconnected struts and a plurality of anchor members extending radially outward from the plurality of interconnected struts in the expanded configuration;

wherein each anchor member of the plurality of anchor members includes a base portion fixedly attached to the plurality of interconnected struts and an anchor tip portion;

wherein the anchor tip portion includes a central penetrating element extending in a first direction and a concave tissue support element that extends circumferentially all of the way around and radially outward from the central penetrating element, wherein the concave tissue support element has an upper surface facing the first direction, the upper surface having a plurality of notches formed therein, wherein the plurality of notches are spaced apart around a circumference of the concave tissue support element;

wherein the concave tissue support element is configured to be non-penetrating.

13. The medical device system of claim 12, wherein the medical implant includes an occlusive element secured to the expandable framework.

14. The medical device system of claim 12, wherein the concave tissue support element is configured to prevent the central penetrating element from penetrating completely through a wall of the left atrial appendage.

15. A medical implant for occluding a left atrial appendage, comprising:

an expandable framework configured to shift between a collapsed configuration and an expanded configuration;

wherein the expandable framework includes a plurality of interconnected struts and a plurality of anchor members extending radially outward from the plurality of interconnected struts in the expanded configuration;

wherein each anchor member of the plurality of anchor members includes a base portion fixedly attached to the plurality of interconnected struts, an anchor tip portion, and a curved portion extending radially outward from the base portion to the anchor tip portion when the expandable framework is in the expanded configuration;

wherein the anchor tip portion includes a central penetrating element extending in a first direction and configured to penetrate into a wall of the left atrial appendage and a tissue support element that extends circumferentially all of the way around and radially from the central penetrating element, wherein the tissue support element has an upper surface facing the first direction, the upper surface having a plurality of notches formed therein, wherein the plurality of notches are spaced apart around a circumference of the tissue support element, the tissue support element configured to engage the wall of the left atrial appendage;

wherein the anchor tip portion is devoid of any element configured to penetrate into the wall of the left atrial appendage other than the central penetrating element.

16. The medical implant of claim 15, wherein the central penetrating element has a generally conical shape.

17. The medical implant of claim 15, wherein the tissue support element is symmetric about the central penetrating element.

18. The medical implant of claim 15, wherein the tissue support element includes a concave portion opening toward a free end of the central penetrating element.

19. The medical implant of claim 15, wherein each notch of the plurality of notches opens toward the free end of the central penetrating element, wherein the plurality of notches alternate with a plurality of ridges around the circumference of the tissue support element.

* * * * *